United States Patent
Kessler

(10) Patent No.: US 8,412,468 B1
(45) Date of Patent: Apr. 2, 2013

(54) METHOD AND APPARATUS FOR WAVELET BASED ELEMENTAL SPECTRUM ANALYSIS

(75) Inventor: Bruce Kessler, Bowling Green, KY (US)

(73) Assignee: Western Kentucky University, Bowling Green, KY (US)

( * ) Notice: Subject to any disclaimer, the term of this patent is extended or adjusted under 35 U.S.C. 154(b) by 203 days.

(21) Appl. No.: 12/756,991

(22) Filed: Apr. 8, 2010

Related U.S. Application Data

(60) Provisional application No. 61/167,613, filed on Apr. 8, 2009.

(51) Int. Cl.
- G01N 31/00 (2006.01)
- G01N 23/00 (2006.01)
- G01N 23/09 (2006.01)
- G06F 17/18 (2006.01)

(52) U.S. Cl. .............. 702/28; 702/22; 702/27; 702/179

(58) Field of Classification Search .......... 702/28, 702/22, 27, 57, 66, 179; 250/282, 287, 288; 356/58, 454
See application file for complete search history.

(56) References Cited

U.S. PATENT DOCUMENTS

| | | | |
|---|---|---|---|
| 5,537,344 A | 7/1996 | Isshiki et al. | |
| 5,870,691 A | 2/1999 | Partyka et al. | |
| 6,038,579 A | 3/2000 | Sekine | |
| 6,208,951 B1 | 3/2001 | Kumar et al. | |
| 6,542,836 B1 | 4/2003 | Sasaki et al. | |
| 6,631,343 B1 | 10/2003 | Kojima | |
| 6,751,564 B2 | 6/2004 | Dunthorn | |
| 6,763,322 B2 | 7/2004 | Potyrailo et al. | |
| 6,826,513 B1 | 11/2004 | Kumar et al. | |
| 6,957,172 B2 | 10/2005 | Wegerich | |
| 6,983,213 B2 | 1/2006 | Wang | |
| 6,985,815 B2 | 1/2006 | Castagna et al. | |
| 7,019,826 B2 | 3/2006 | Vook et al. | |
| 7,248,370 B2 | 7/2007 | Jones | |
| 7,251,037 B2 | 7/2007 | Jones | |
| 7,254,500 B2 | 8/2007 | Makeig et al. | |
| 7,425,700 B2 | 9/2008 | Stults et al. | |
| 7,493,225 B2 | 2/2009 | Wang et al. | |
| 7,496,619 B2 * | 2/2009 | Aldroubi et al. | 708/446 |
| 7,702,502 B2 * | 4/2010 | Ricci et al. | 704/205 |
| 2007/0054266 A1 | 3/2007 | Sato et al. | |

OTHER PUBLICATIONS

Bruce, Kessler; An Orthogonal Scaling Vector Generating a Space of C1 Cubic Splines Using Macroelements; Journal of Concrete and Applicable Mathematics; 2004; USA.

\* cited by examiner

*Primary Examiner* — Michael Nghiem
*Assistant Examiner* — Ricky Ngon
(74) *Attorney, Agent, or Firm* — Middleton Reutlinger; Scott W. Higdon; John F. Salazar

(57) ABSTRACT

A method and apparatus for wavelet based elemental spectrum analysis is described. The system and method set forth allows for elemental decomposition of sampling spectral data to determine the presence of materials in the interrogated object. The method utilized and set forth implements wavelet decomposition of a spectrum and elemental analysis without requiring an empty background spectrum for subtraction of the background noise from the sampling spectrum. The system and method measures the presence of elements present in the sample being analyzed. The system may also measure the ratio of elements present in the sample being analyzed.

19 Claims, 25 Drawing Sheets

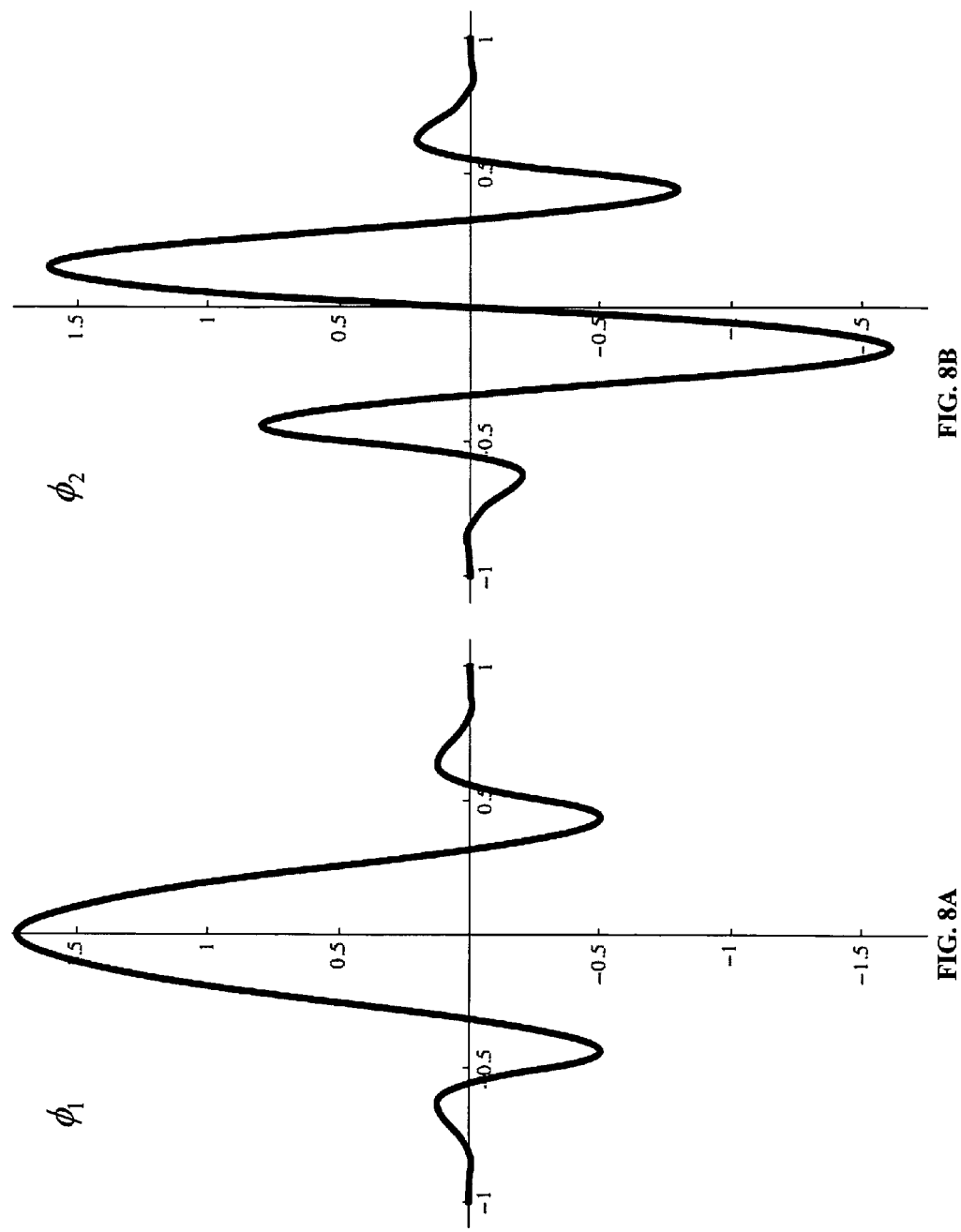

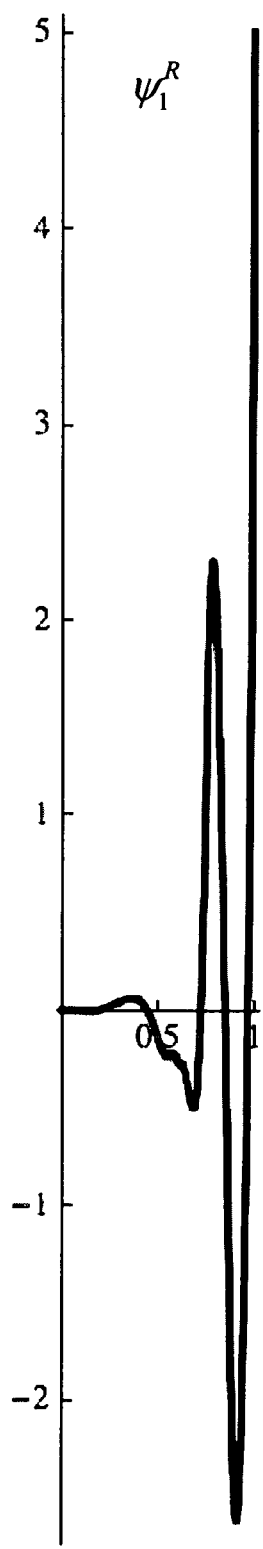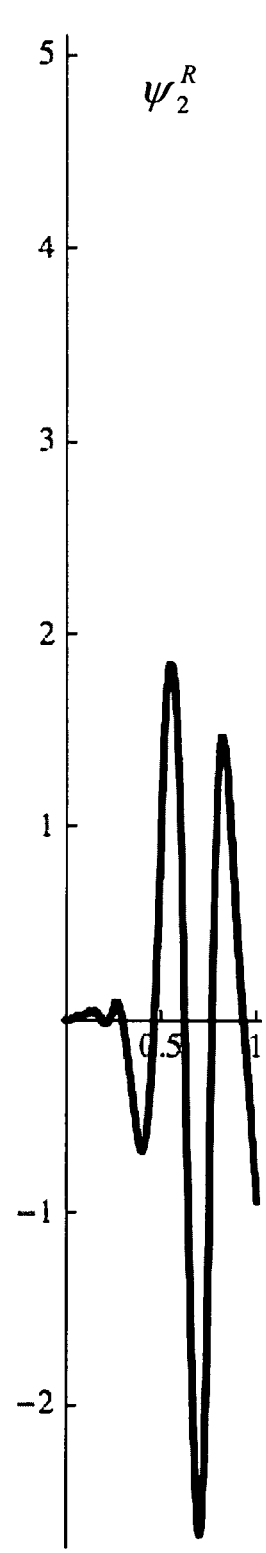
FIG. 11C   FIG. 11D

METHOD AND APPARATUS FOR WAVELET BASED ELEMENTAL SPECTRUM ANALYSIS

CROSS-REFERENCE TO RELATED DOCUMENTS

This Application claims the benefit of currently pending Provisional Application Ser. No. 61/167,613 filed Apr. 8, 2009, entitled Method and Apparatus for Wavelet Based Elemental Spectrum Analysis, which is hereby incorporated by reference in its entirety.

TECHNICAL FIELD

The present invention is directed towards a method and apparatus for detection and determination of elemental composition of a test material through the use of wavelet decomposition of a spectrum. The method and apparatus may identify the presence and ratios of elements in the sample being interrogated.

SUMMARY

Generally, in one aspect a method of pre-filtering and analyzing spectral data for the detection of elemental signatures in an interrogated object using multi-wavelet filters is provided. The method includes pre-filtering data of gamma ray counts obtained from bombardment of an interrogated object in order to maintain polynomial order using a quasi-interpolation prefilter, wherein the pre-filtering converts the data into pre-filtered signal data. The method further includes generating an orthogonal matrix coefficient of scaling vector $\Phi=(\phi_1, \phi_2, \phi_3, \phi_4)^T$ to construct filters for multi-wavelet decomposition of the prefiltered signal data, wherein the scaling vector $\Phi=(\phi_1, \phi_2, \phi_3, \phi_4)^T$ substantially satisfies the solution:

$$\Phi(x) = \left| \sqrt{2} \sum_{i=-2}^{1} g_i \Phi(2x-i) \right.$$

and has a left boundary function $$\phi_1^L = \frac{\phi_1|_{[0,1]} - \frac{\langle \phi_1|_{[0,1]}, \phi_2|_{[0,1]} \rangle}{\phi_2|_{[0,1]}, \phi_2|_{[0,1]}} \phi_2 \Big|_{[0,1]}}{\left\| \phi_1|_{[0,1]} - \frac{\langle \phi_1|_{[0,1]}, \phi_2|_{[0,1]} \rangle}{\phi_2|_{[0,1]}, \phi_2|_{[0,1]}} \phi_2 \Big|_{[0,1]} \right\|} \text{ and } \phi_2^L = \sqrt{2} \, \phi_2|_{[0,1]}$$

and a right boundary function $\phi_1^R(x) = \phi_1^L(1-x)$ and $\phi_2^R = -\phi_2^L(1-x)$. The method further includes constructing a multi-wavelet for the scaling vector $\Phi=(\phi_1, \phi_2, \phi_3, \phi_4)^T$, the multi-wavelet being associated with the scaling vector $\Phi=(\phi_1, \phi_2, \phi_3, \phi_4)^T$ and having matrix coefficients substantially satisfying the equation $$\psi(x) = \sqrt{2} \sum_{i=-2}^{1} h_i \Phi(2x-i),$$

the multi-wavelet having a left boundary function of $$\begin{bmatrix} \psi_1^L \\ \psi_2^L \end{bmatrix}(x) = h_0^L \begin{bmatrix} \phi_1^L \\ \phi_2^L \\ \phi_3 \\ \phi_4 \end{bmatrix}(2x) + h_1^L \Phi(2x-1),$$

and a right boundary function of $$\begin{bmatrix} \psi_1^R \\ \psi_2^R \end{bmatrix}(x) = h_0^R \Phi(2x) + h_1^R \Phi(2x-1) + h_2^R \begin{bmatrix} \phi_1^R \\ \phi_2^R \end{bmatrix}(2x-1), .$$

The method further includes interpolating the multi-wavelet for comparison with an elemental database to identify elements and element concentrations in the interrogated object.

In some embodiments the prefiltered signal data is decomposed to a user selected level of decomposition utilizing the multi-wavelet. In versions of these embodiments the user selected level of decomposition is based on the curvature of underlying background distortion of the data. In versions of these embodiments level of decomposition is bound by a maximum level of decomposition.

Generally, in another aspect a method for determining elements of an interrogated object is provided and includes storing a library database of response spectra for various elements of interest, irradiating an object to create neutron reactions, generating a data spectrum by detecting the gamma rays emitted by the object, and recognizing the individual elements contained in the data spectrum by the following steps:

generating a matrix coefficient of scaling vectors to construct filters for wavelet decomposition; wherein the matrix coefficient substantially satisfies the dilation equation:

$$\Phi(x) = \left| \sqrt{2} \sum_{i=-2}^{1} g_i \Phi(2x-i) \right.$$

of the scaling vector $\Phi=(\phi_1, \phi_2, \phi_3, \phi_4)^T$; wherein the filters are orthogonal multiwavelet filters; creating an analysis window for the elements of interest; prefiltering the data spectrum over the analysis window, thereby creating an original data set; decomposing the original data set utilizing the orthogonal multiwavelet filters to a level of decomposition, thereby creating a wavelet decomposition data set; replacing the wavelet decomposition data set with a calculated linear combination of a wavelet decomposition for each of the elements of interest, thereby creating an altered decomposed data set; reconstructing the altered decomposed data set, thereby creating a reconstructed data set; determining coefficients that minimize the sum of the squares of the differences between interpolation points of the reconstructed data set and interpolation points of the original data set; creating a least squares fit between interpolation points of the original data set and the reconstructed data set based on the coefficients; converting the least squares fit into a set of basis coefficients to create a vector of element amounts showing the relative amounts of each of the elements of interest in the test material; and identifying the angle θ between the vector of element amounts and at least one of vectors associated with the elements of interest and subspaces generated by the vectors associated with the elements of interest.

In some embodiments the angle θ is found by: θ=cos⁻¹ [(the vector of element amounts·the vectors associated with the elements of interest)/(‖the vector of element amounts‖ ‖the vectors associated with the elements of interest‖]).

In some embodiments the method further includes the step of adjusting a peak center of at least one of the elements of interest. In versions of these embodiments the step of adjusting a peak center of at least one of the elements of interest includes calculating a center of mass of an adjusted elemental spectra data set. In versions of these embodiments the adjusted elemental spectra data set is generated by subtracting a decomposed elemental spectra data set from an original elemental spectra data set. The decomposed elemental spectra data set may be obtained utilizing the orthogonal multiwavelet filters.

Generally, in another aspect a method for determining elements in spectral data corresponding to an interrogated object is provided and includes the following steps: storing a library database of response spectra for various elements of interest; adjusting a peak center of at least one of the elements of interest; storing a level of decomposition; receiving raw spectral data corresponding to properties of an object interrogated at a plurality of energy levels; prefiltering a sample from a spline that interpolates the raw spectral data, thereby creating an original data set; wherein the prefiltering utilizes a non-orthogonal quasi-interpolation prefilter; decomposing the original data set to the level of decomposition, thereby creating a wavelet decomposition data set; wherein the decomposing utilizes orthogonal multiwavelet filters; replacing the wavelet decomposition data set with a calculated linear combination of a wavelet decomposition for each of the elements of interest, thereby creating an altered decomposed data set; reconstructing the altered decomposed data, thereby creating a reconstructed data set; determining coefficients that minimize the sum of the squares of the differences between interpolation points of the reconstructed data set and interpolation points of the original data set; creating a least squares fit between interpolation points of the original data and the reconstructed data based on the coefficients; converting the least squares fit into a set of basis coefficients to create a vector of element amounts showing the relative amounts of each of the elements of interest in the test material; and identifying the angle θ between the vector of element amounts and at least one of vectors associated with the elements of interest and subspaces generated by the vectors associated with the elements of interest.

Generally, in another aspect, a computer program product may be provided that includes a computer usable medium having a computer readable program code embodied therein. The computer readable program code may be adapted to implement a method to determine elements in spectral data corresponding to an interrogated object.

Generally, in another aspect a computer system may be provided that implements a method to determine elements in an interrogated. The computer system may include a controller in electrical communication with memory, a data input, and a data output. The memory may store a computer program implements the method and the controller may execute said computer program. The data input may receive spectral data for analysis from one or more external sources. The controller may analyze the spectral data to detect at least one elemental signature in the spectral data. At least one elemental signature detected by the controller may be communicated to a user via the data output and/or may be communicated to another apparatus via the data output.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, a mouse, keyboard, keypad, various types of game controllers (e.g., joysticks), track balls, display screens, various types of graphical user interfaces (GUIs), touch screens, microphones and other types of sensors that may receive some form of human-generated stimulus and generate a signal in response thereto.

The term "controller" is used herein generally to describe various apparatus relating to the determination of elemental composition of a test material. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIGS. 8A through 8D illustrate individual elements of the orthogonal scaling vector $\phi$.

FIGS. 11A through 11D illustrate boundary functions $\psi_1^L$, $\psi_2^L$, $\psi_1^R$, and $\psi_2^R$, respectively.

DETAILED DESCRIPTION OF THE PREFERRED EMBODIMENT

Figure 1:
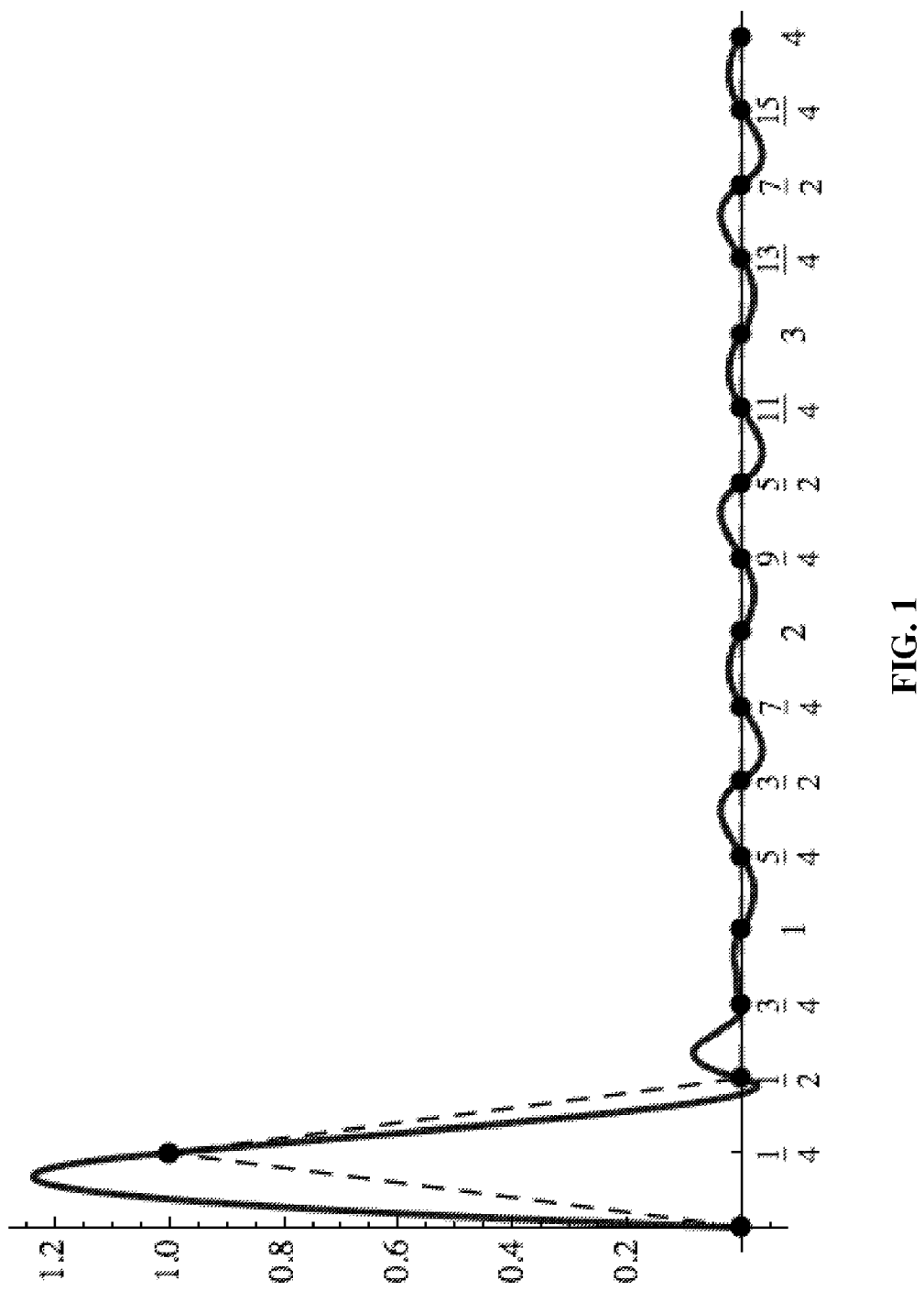
FIG. 1 illustrates a representative function in the approximation space when using an interpolation prefilter on a sample data set with one nonzero value.

It is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," "in communication with" and "mounted," and variations thereof herein are used broadly and encompass direct and indirect connections, couplings, and mountings. In addition, the terms "connected" and "coupled" and variations thereof are not restricted to physical or mechanical connections or couplings.

Furthermore, and as described in subsequent paragraphs, the specific mechanical configurations illustrated in the drawings are intended to exemplify embodiments of the invention and that other alternative mechanical configurations are possible.

High explosives and illicit drugs are primarily composed of the chemical elements of hydrogen, carbon, nitrogen and oxygen. Systems for the detection of these elements are fairly well known. These systems utilize the irradiation of such material by neutrons and detection of gamma photons emitted by the materials after subjecting them to said neutron burst. One technique of such detection is neutron activation analysis. These prior art devices utilize the known effect of gamma ray emission from the nucleus of the objects being interrogated after irradiation. The concentration of these gamma rays can be detected by gamma ray detectors and the signals analyzed to determine the concentrations of chemical elements which make up the object being interrogated. These elements are found in explosives or illicit drugs in differing quantities, ratios and concentrations. By calculating and determining said ratios and concentrations, it is possible to identify and differentiate drugs and other contraband from sugar or other materials by measuring the amount of hydrogen, carbon or other material contained in the interrogated object. It is understood that the process of producing gamma photons by the interaction of the nucleus of the inspected material with neutrons from a neutron generator can be effected by various processes. These various processes include fast neutron, thermal neutron, and neutron activation reactions.

Thermal neutron reactions occur by the capture of a neutron by a nucleus producing an isotope which is de-excited by the emission of gamma radiation. Fast neutron reactions result in the inelastic scattering of a neutron on a nucleus which is de-excited by the emission of prompt gamma radiation, this interaction occurring only with fast neutrons having a high enough energy which is at least equal to that of the prompt gamma radiation. Finally, neutron activation reactions occur by the activation of a nucleus by a thermal or fast neutron which creates a radioactive nucleus having a certain life and which disintegrates thereby emitting activation gamma radiation. Further, prior art devices which are disclosed in U.S. Pat. Nos. 5,293,414; 4,864,142; 5,373,538; 5,982,838; 6,438,189 and 6,563,898, all incorporated herein by reference, suffer from other problems including the nonportability of their devices and the effect of producing false positive results when interrogating the object. Such false positives can occur due to background radiation, failure to account for the orientation of the interrogated object and detectors, and the statistical analysis which may cause a miscalculation of the occurrence of the appropriate materials. Most importantly, the need for an accurate system for emission and detection of neutrons and gamma rays has been needed in order to properly allow the detection of explosives and other material in varying environmental situations and circumstances.

It is understood that other materials besides drugs and contraband may also be identified utilizing the system and algorithm described herein. It is further understood that although the figures and descriptions herein may reference gamma ray counts at different energy levels, such description is not limiting. The system and algorithm described herein can be utilized in conjunction with any type of spectroscopy where particle counts are made at different frequencies or energy levels. For example, the algorithm may be used in conjunction with fluorescence, X-ray, and radio telescope spectroscopy.

The system and method of the present invention utilizes wavelet decomposition of a spectrum and the Gaussian peaks associated with the elements and identifies first the underlying distortion of the data and then measures the presence and ratios of elements present in the sample being analyzed. Other than initially establishing the library of elements being considered and the library of possible compounds expected to be found, the system and method of the present invention enables not necessitating prompting as to the shape of the data and the locations of the elemental representations in the data. Generally, the method and system of the present invention utilizes an automated system for analyzing spectral data while also removing the necessity of background spectrum subtraction. Further, the system presently described utilizes wavelet decomposition techniques in matching patterns of spectral data for compositional determination. The system set forth separates noise from the actual derived signal and utilizes multiwavelets for compositional determination. Particularly for accurate matching of spectral data, orthogonal multiwavelet decomposition is utilized with autonomous identification of elemental signatures in the analysis of mass spectrometry data.

Wavelets have previously been used to find patterns in a stream of raw data. For example, single wavelets can be applied to the raw data with no need for prefiltering. However, such wavelets may not be very useful on bounded data for one or more reasons. For example, truncating a single wavelet removes their orthogonality to their translates and simply padding outside the window alters the wavelet decomposition of the bounded signal, which may no longer match the target pattern's decomposition.

Algorithm Prefiltering

Also, using multiwavelets in applications may require that the raw data be prefiltered. Prefiltered means that the data must be converted into coefficients of the basis functions being used to represent the signal. Ideally, a prefilter associated with a scaling vector should be invertible, preserve the polynomial order of the data up to the approximation order of the basis (that is, data sampled from a polynomial that is in the approximation space of the basis should get mapped to the basis coefficients that would give that polynomial), maintain symmetries of the original data, and be orthogonal (that is, the basis coefficients created should have the same norm as the original data).

Prefilters with all these qualities may be difficult to construct, thereby causing many applications to still use single wavelets. An interpolation prefilter, which maps data to the coefficients of basis functions whose sum will pass through the data values, is an invertible prefilter that is relatively easy to construct. The interpolation prefilter will preserve polynomial order and maintain symmetries of the original data. One disadvantage with the interpolation prefilter is that it is generally not orthogonal. An additional disadvantage of the interpolation prefilter is that, due to the lack of corners in the functions in its approximation space, a variation in data in one part of the signal will cause a "wiggle" throughout the prefiltered data, as illustrated in FIG. 1. FIG. 1 illustrates a representative function (solid line) in the approximation space when using an interpolation prefilter on a sample data set (dashed line) with one nonzero value.

Figure 2A:
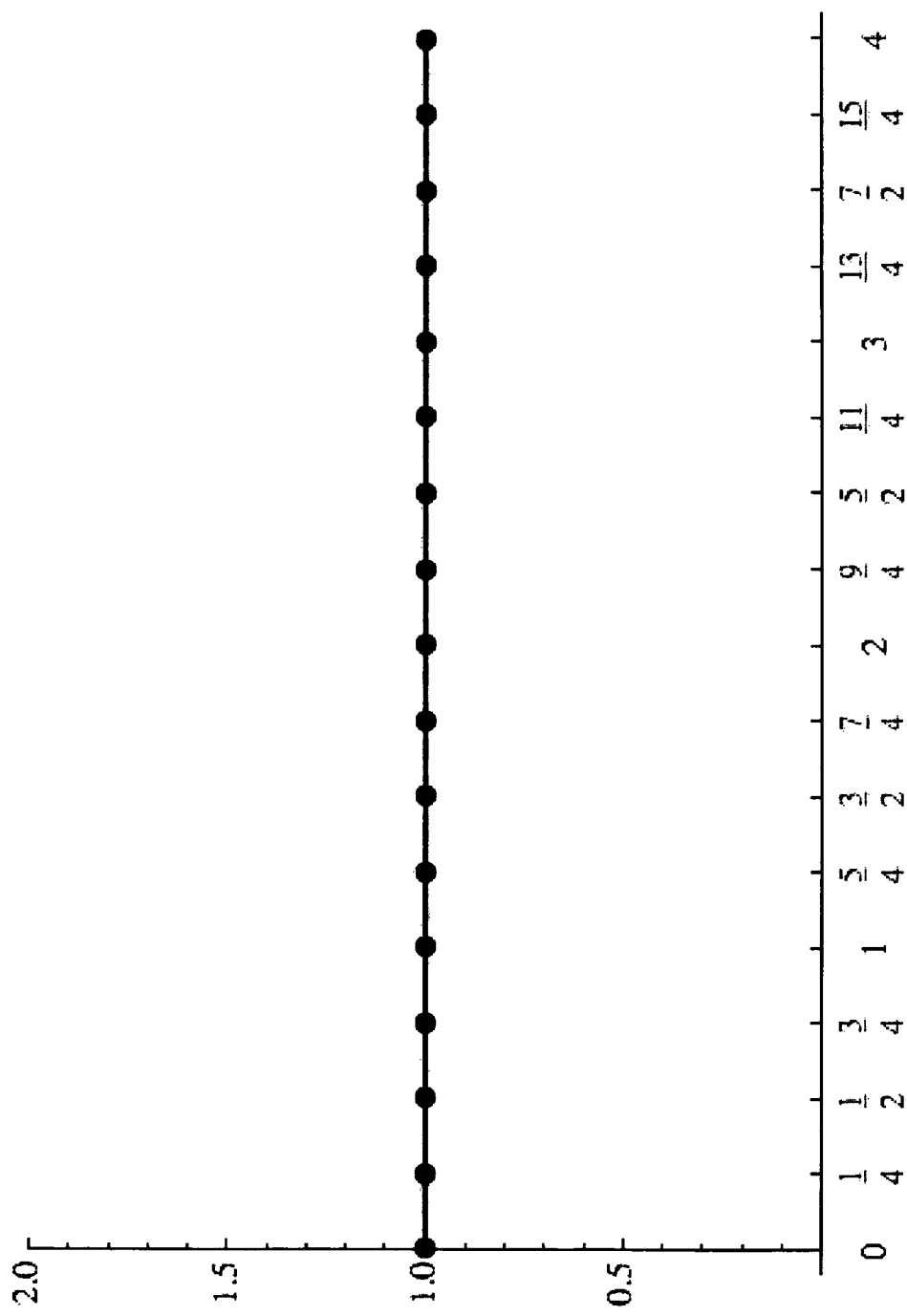
FIG. 2A illustrates the representative function in the approximation space when using the quasi-interpolation prefilter on a data set sampled from a constant function.
Figure 2B:
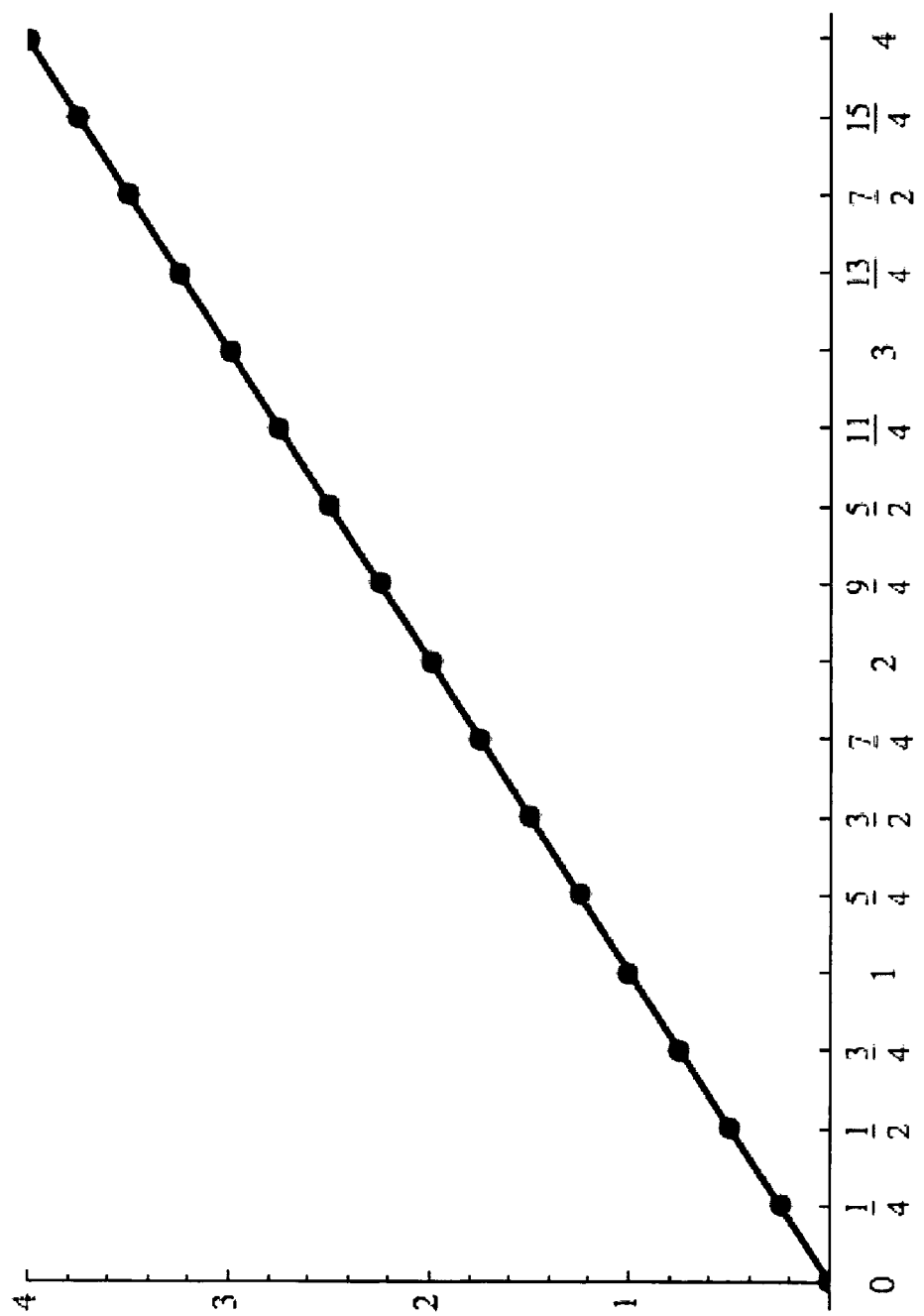
FIG. 2B illustrates the representative function in the approximation space when using the quasi-interpolation prefilter on a data set sampled from a linear function.
Figure 2C:
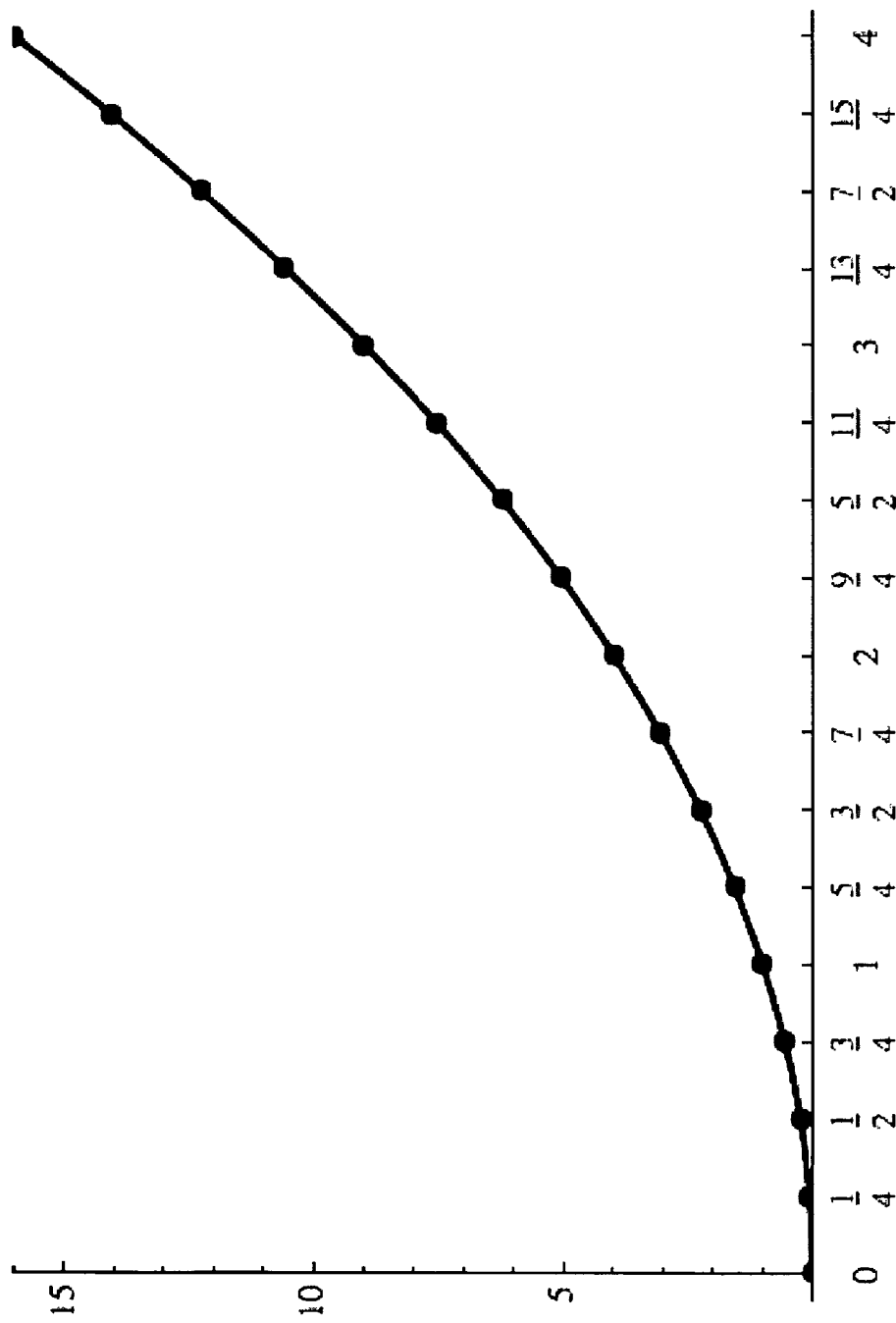
FIG. 2C illustrates the representative function in the approximation space when using the quasi-interpolation prefilter on a data set sampled from a quadratic function.
Figure 2D:
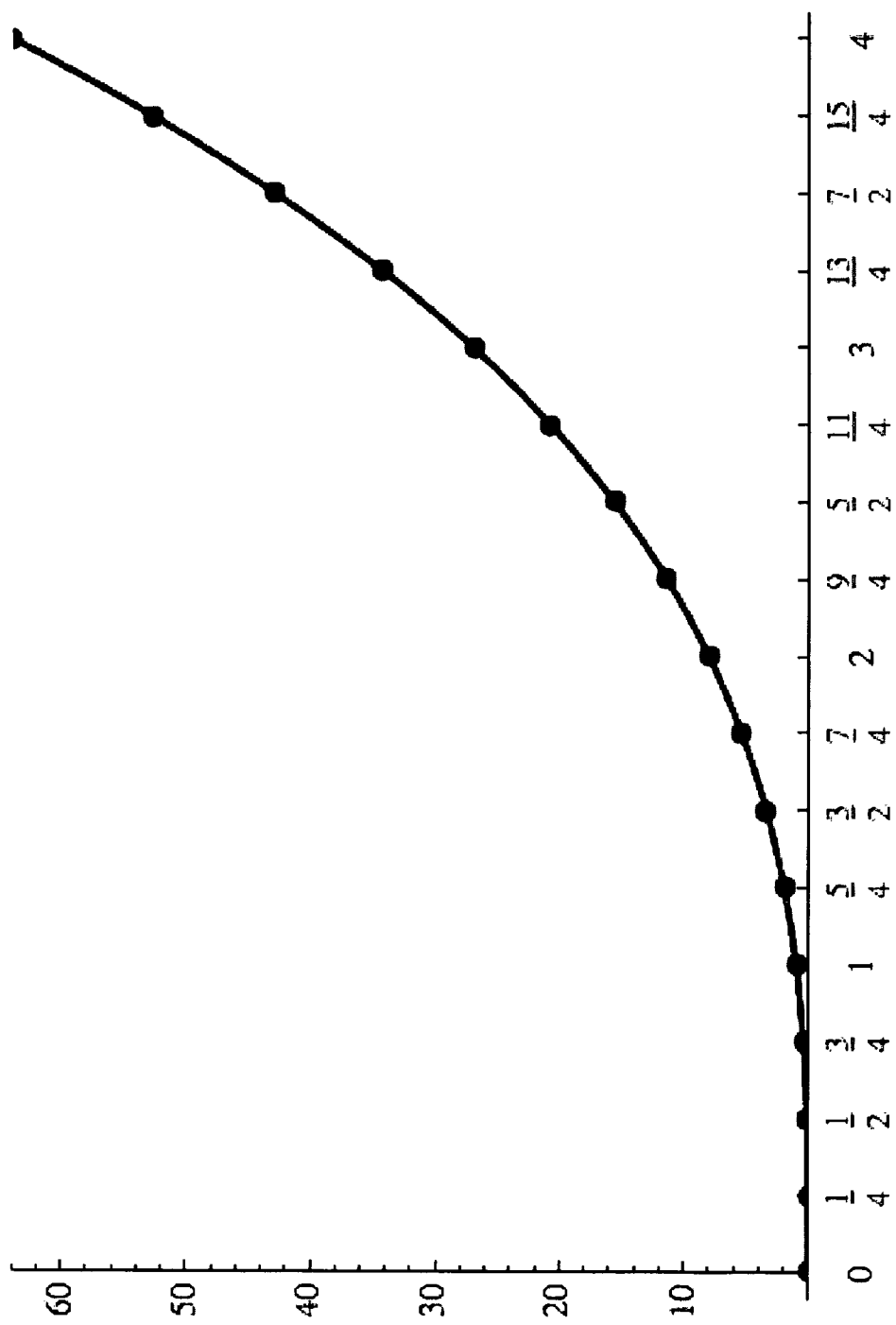
FIG. 2D illustrates the representative function in the approximation space when using the quasi-interpolation prefilter on a data set sampled from a cubic function.
Figure 3A:
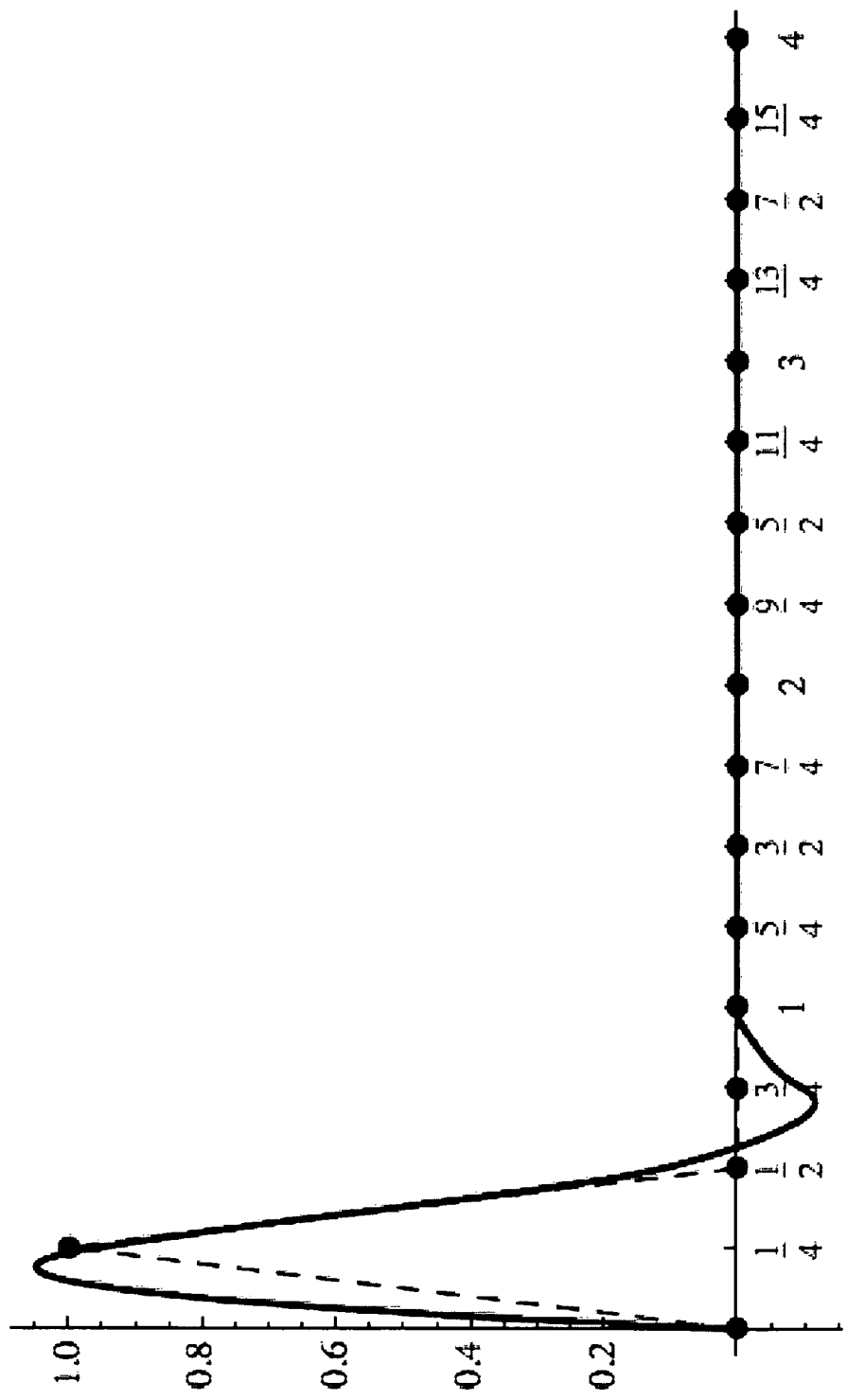
FIG. 3A illustrates the representative function in the approximation space when using the quasi-interpolation prefilter on a sample data set with one nonzero data value.
Figure 3B:
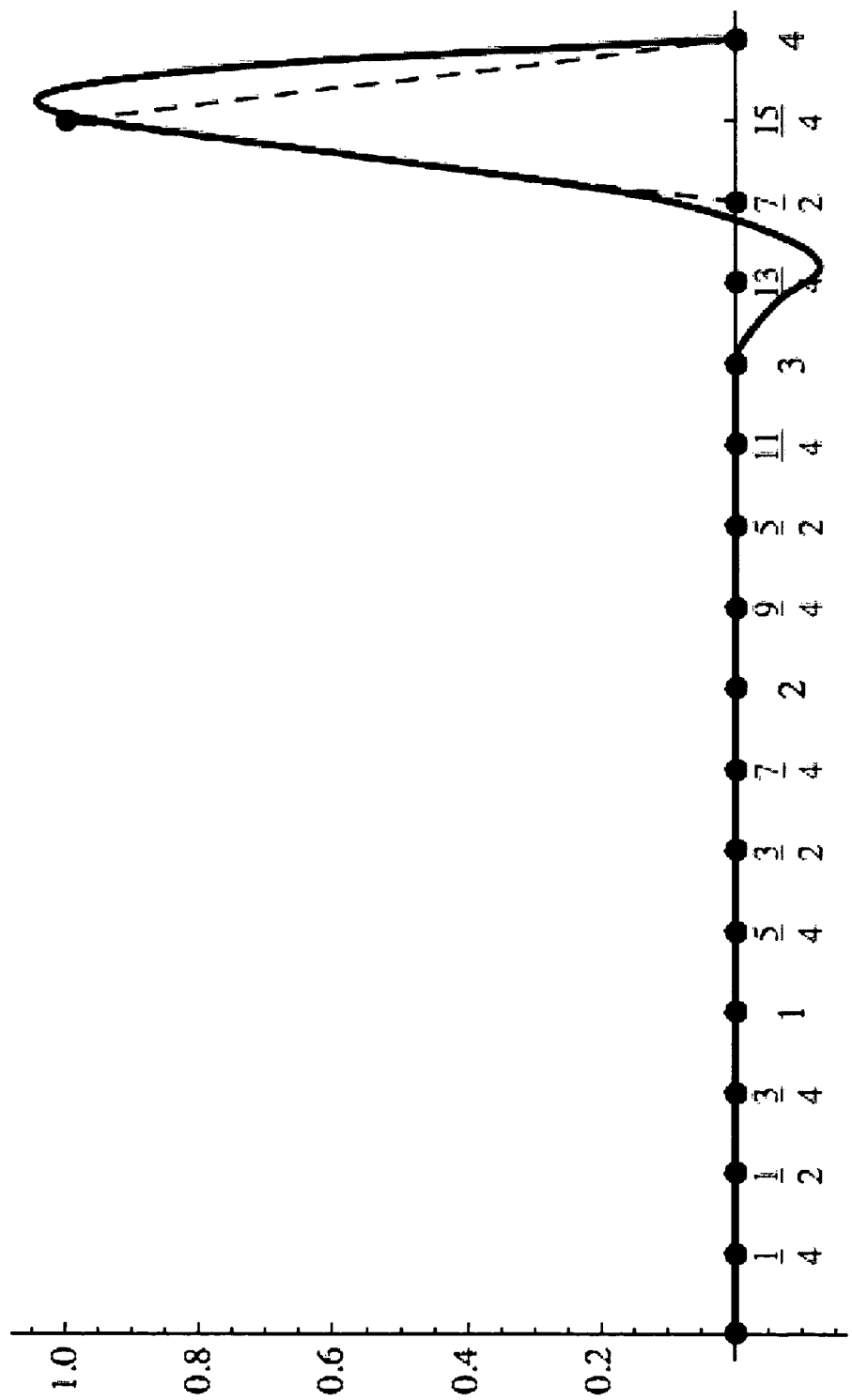
FIG. 3B illustrates the same quasi-interpolation prefilter of FIG. 3A used on the same data in reverse order to generally demonstrate the symmetric properties of the prefilter.

The prefilter in use in embodiments of the algorithm is a quasi-interpolation prefilter, meaning that if the data is sampled from a polynomial that is in the approximation space of the basis, the function that the data is mapped to will interpolate the data, as shown in FIGS. 2A-D. FIGS. 2A-D illustrate the representative function in the approximation space when using the quasi-interpolation prefilter on a data set sampled from a constant function (FIG. 2A), a linear function (FIG. 2B), a quadratic function (FIG. 2C), and a cubic function (FIG. 2D). However, other data will not get mapped to a curve that will necessarily pass through the data values. This allows for a localization of "wiggly" data, as shown in FIGS. 3A and 3B. FIG. 3A illustrates the representative function (solid line) in the approximation space when using the quasi-interpolation prefilter on a sample data set (dashed line) with one nonzero data value. FIG. 3B illustrates the same quasi-interpolation prefilter used on the same data in reverse order.

Figure 4:
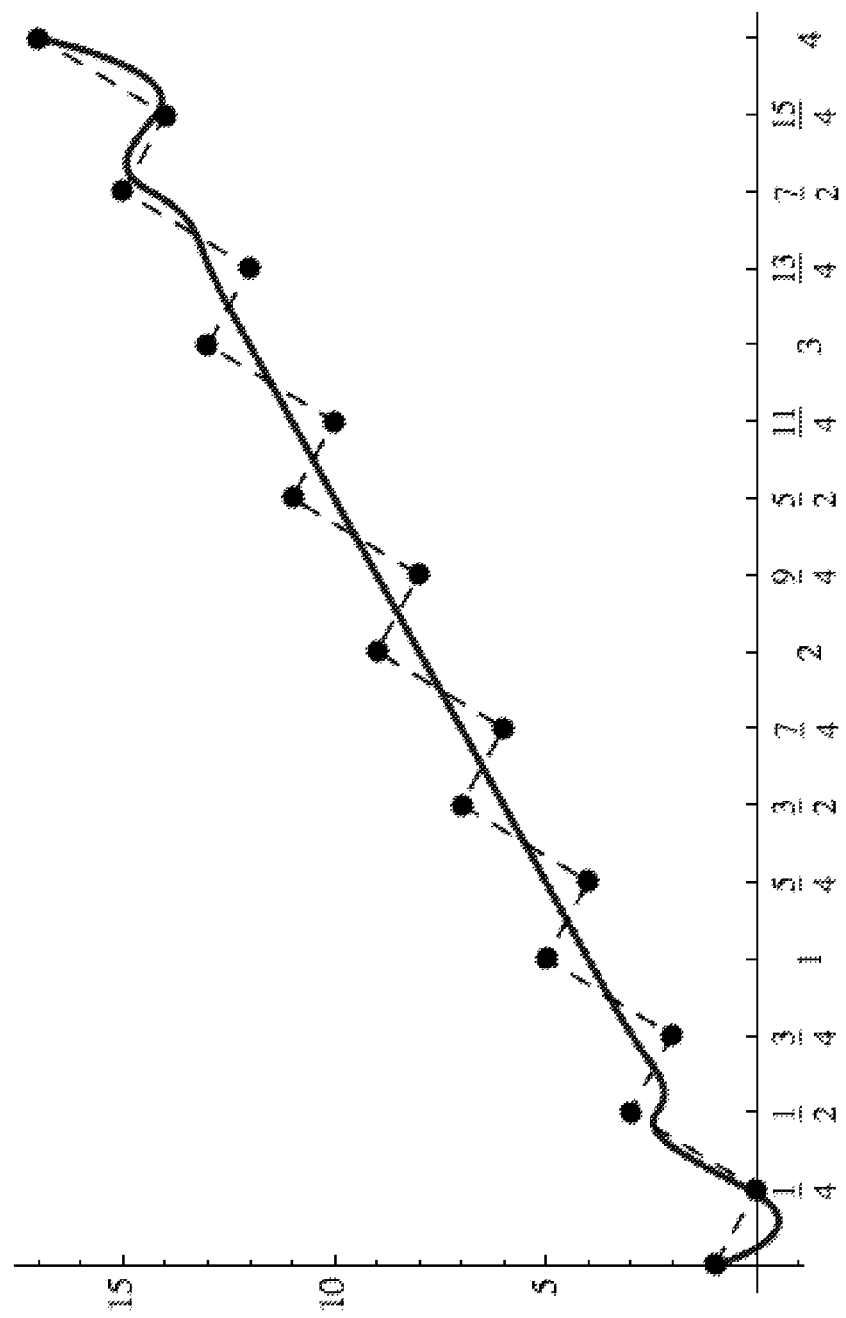
FIG. 4 illustrates the representative function in the approximation space when using the quasi-interpolation prefilter on a data set sampled from a linear function with a constant value alternatively added and subtracted, to generally demonstrate the smoothing properties of the prefilter.
Figure 5:
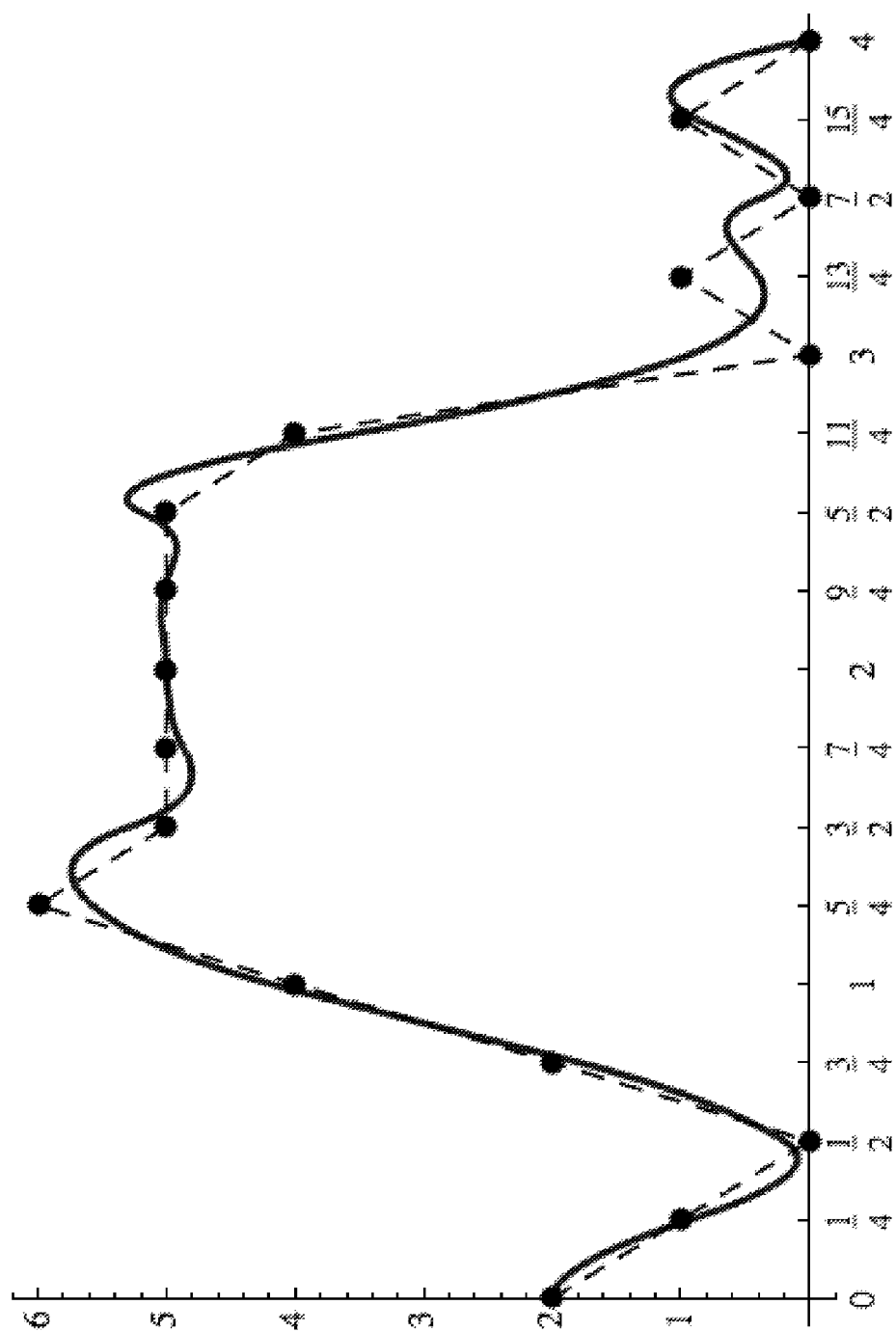
FIG. 5 illustrates the representative function in the approximation space when using the quasi-interpolation prefilter on a sample data set, to generally demonstrate how the prefilter generally maintains the shape of the data.

This quasi-interpolation prefilter has the added benefit of providing a smooth representative curve when the data fluctuates more than can be accommodated by the approximation space. This property is illustrated in FIG. 4, which shows the representative function (solid line) in the approximation space when using the quasi-interpolation prefilter on a data set (dashed line) sampled from a linear function with a constant amount alternatively added and subtracted. The representative function of FIG. 4 generally holds the shape of the data, but does not necessarily interpolate, as shown with a sample data set in FIG. 5. FIG. 5 illustrates the representative function (solid line) in the approximation space when using the quasi-interpolation prefilter on a sample data set (dashed line). The quasi-interpolation prefilter is not invertible or orthogonal, but those properties are not necessarily needed in the algorithm described herein.

Finding Patterns in the Algorithm

The general approach for finding patterns in data is to create a target wavelet decomposition from the pattern for which one is searching and then take the wavelet decompositions from an equal-length substrings of the data, sliding over the length of the original data set. If the wavelet decomposition is within some tolerance of the target wavelet decomposition, then the pattern is "found." This general approach may be a perfectly valid approach when using a single wavelet, or when using multiwavelets with an orthogonal prefilter, since the root mean square error of the wavelet coefficients is representative of the error in the actual signal.

However, in embodiments of the algorithm that do not use an orthogonal prefilter, a different approach may be taken to measure the closeness of a fit. In particular, the signal can be put back together (reassembled) with a linear combination of the wavelet decompositions of the elements in an elemental library. The coefficient values for each of the different elements that minimize the sum of the squares of the differences between the reassembled data can then be solved for and the points sampled from the identical locations of the representative curve produced by the quasi-interpolation prefilter in the approximation space.

Advantages of measuring the closeness of the fit in this fashion include a lack of needing to use an orthogonal prefilter to get a fair representation of how closely the pattern is being matched. Moreover, by comparing to the representative curve interpolation points, there is not a need to invert the quasi-interpolation prefilter to compare the reconstructed data. The coefficients are postfiltered with the inverse of the interpolation prefilter, and compared to the identically located representative curve interpolation points.

Step-by-Step Description of an Embodiment of the Algorithm

Provided below is a step-by-step summary of what takes place in an embodiment of the algorithm presented in the order in which it occurs. The step-by-step summary provided below will be followed by a more detailed explanation of an embodiment of the algorithm.

Figure 6:
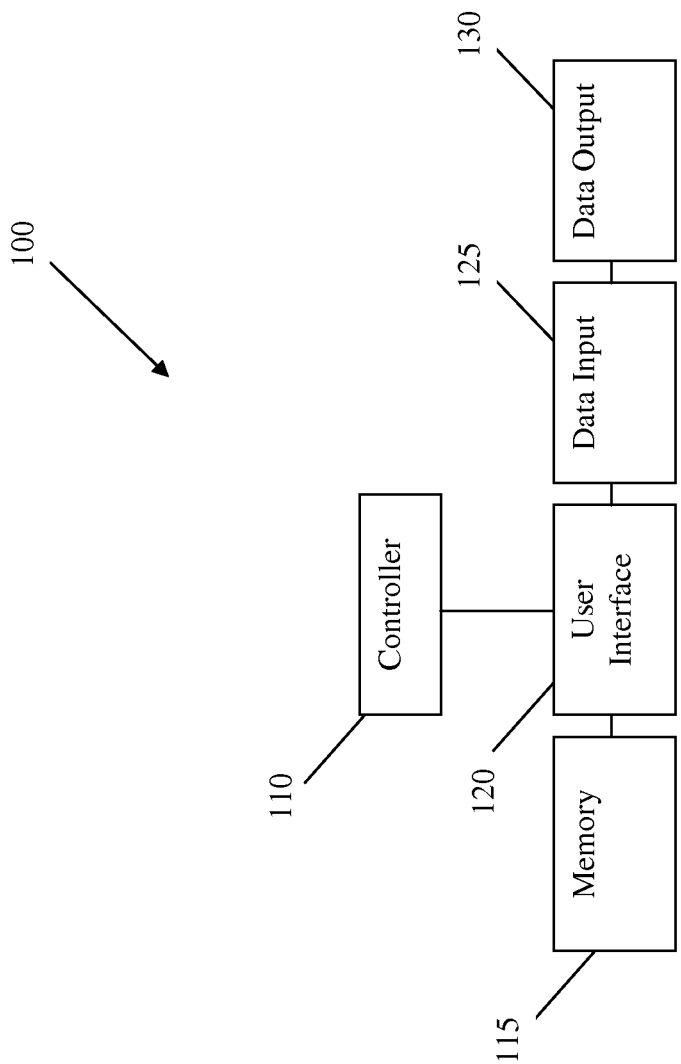
FIG. 6 illustrates an embodiment of an apparatus for prefiltering and analyzing spectral data.

In some embodiments the algorithm described herein may be implemented in a computer program, stored in memory, and executed by a controller For example, with reference to FIG. 6, an embodiment of an apparatus for prefiltering and analyzing spectral data 100 is depicted. The apparatus 100 includes a controller 110 in electrical communication with memory 115, a user interface 120, a data input 125, and a data output 130. The memory 115 may store a computer program that includes the algorithm described herein and the controller 110 may execute said computer program. The data input 125 may receive data for analysis from one or more external sources. For example, the data input 125 may be in electrical communication with a gamma ray detector that feeds raw spectral data to the controller 110 or a storage medium containing raw spectral data. The controller 110 may optionally store the raw spectral data in memory 115 and analyze the data in accordance with an embodiment of the algorithm described herein to detect at least one elemental signature in the raw spectral data. Data (raw spectral data or other data) may also optionally be entered via user interface 120. Information indicative of the at least one elemental signature that is detected by the algorithm in the raw spectral data may be communicated to a user via the data output 130 (e.g., a screen, array of LEDs, audio device). For example, in some embodiments one or more elements and/or compounds and the conformity of the elements and/or compounds to the raw spectral data may be presented to a user on a monitor. Information indicative of the at least one elemental signature detected by the algorithm in the raw spectral data may additionally or alternatively be communicated to another apparatus via the data output 130 (e.g., a data transmitter utilizing wired or wireless communication) for further action to be taken based on the elemental signature specifics.

Figure 7:
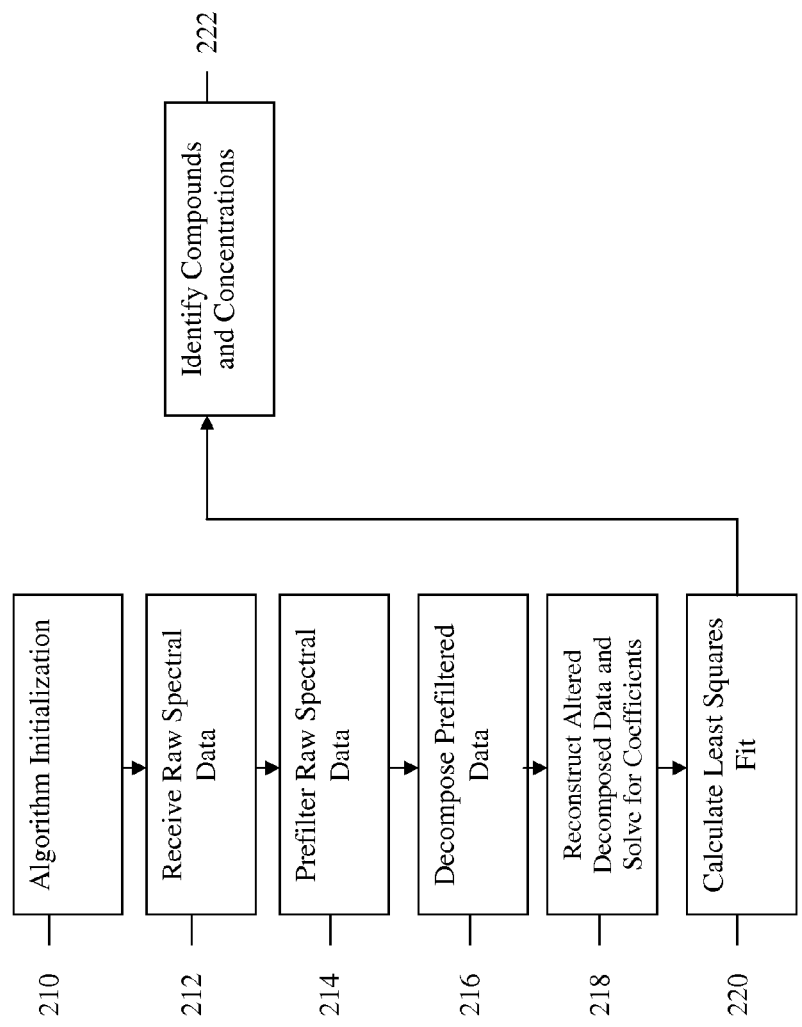
FIG. 7 illustrates an overview of the steps of an embodiment of the algorithm.

Referring now to FIG. 7, an overview of the steps of an embodiment of the algorithm is shown. At step 210 initialization of the algorithm takes place. As part of the initialization of the algorithm, information regarding the peak locations and relative peak heights for equal masses of the different elements to be searched are programmed into the algorithm. A search threshold and decomposition level may also be inputted into the algorithm in order to fine-tune the location of the peaks in the data. The search threshold may be dependent on the perceived accuracy of the calibration of the device collecting the data (e.g., a gamma ray detector) and/or the proximity of the peaks for the elements that are being searched. The level of decomposition may be dependent upon the curvature of the underlying background distortion of the data. The search threshold and/or the level of decomposition may be manually inputted by a user.

To fine-tune the location of the peaks, raw spectral data is received and fit with a cubic spline, and samples at uniform intervals from the left edge of the leftmost peak of the data to the right edge of the rightmost peak of the data are taken. The samples are then prefiltered using the quasi-interpolation prefilter described herein, and a wavelet decomposition of the prefiltered data is performed to a chosen level of decomposition. A default level of decomposition may be a full decomposition to the smoothest level, but if the smoothest approximation generated is determined by a user to not match the general background shape of the data, then the user may choose to reapply the algorithm, specifying a lower level of decomposition to better match the data.

This smoothest approximation generated is then subtracted from the original raw data and negative values are set to 0. This "adjusted" set of data will be used to statistically reset peak centers. For each given peak location, adjusted data points within the user-defined threshold around each given peak location are collected. The number of data points that would fall within 6 standard deviations is calculated, and the sums of the adjusted data values over data intervals of that number are found. On the subinterval of the adjusted data with the maximum sum, the center of mass of that data is statistically calculated, and the peak location is reset to that amount. In the event that all of the adjusted data values are zero, the peak location remains the user-input amount.

Once the peak locations are adjusted for all of the user-input elements, the wavelet decompositions are constructed for each element to be searched. The wavelet decompositions are constructed to the chosen level of decomposition. The wavelet decompositions are found over an interval from the left edge of the leftmost elemental peak to the right edge of the rightmost elemental peak. These wavelet decompositions are also programmed into the algorithm. Also as a part of the initialization of the algorithm, information regarding the relative amounts of the elements being searched for in each of the various substances that should be identifiable may be fed into the algorithm.

At step 212 raw spectral data is received and fit with a cubic spline for uniform sampling as described in step 210. The raw spectral data may be received, for example, indirectly from a radiation detector receiving emitted radiation from an interrogated object. The raw spectral data may optionally be stored in memory. As will be appreciated by one of ordinary skill in the art having had the benefit of the present disclosure, the raw spectral data received in this step, and/or in other steps of the algorithm, may be subjected to some degree of filtering by an external device (e.g., the controller of the radiation detector).

At step 214 the raw spectral data is prefiltered by the algorithm. Only raw spectral data over the aforementioned interval (interval from the left edge of the leftmost elemental peak to the right edge of the rightmost elemental peak) is analyzed. Since the number of data values over this interval can vary, a fixed-length sample from a cubic spline that interpolates the data is taken. The raw spectral data over this valid interval is then prefiltered using the quasi-interpolation prefilter described herein, including the left-boundary and right-boundary versions of the quasi-interpolation prefilter. The interpolation points of the representative curve of the original data are generated at the same locations as the fixed-length sample from the cubic spline. This prefiltered data will be the new "original signal" to which reconstructed data is compared.

At step 216 the prefiltered data is decomposed and its wavelet decomposition is replaced with a linear combination of the various elements being searched. Accordingly, "altered decomposed data" is created. The wavelet decompositions of this step are constructed to the level of decomposition chosen in step 210.

At step 218 the altered decomposed data is reconstructed and postfiltered using an interpolation postfilter, thereby creating a "reconstructed signal." Coefficients of the elemental wavelet decompositions are then solved for. Namely, coefficients are solved for that minimize the sum of the squares of the differences between the interpolation points of the curve from the reconstructed signal and the interpolation values of the representative curve of the prefiltered data (the original signal).

At step 220 a least squares fit is calculated. The coefficients found at step 218 are used to determine how much of each element's scaling function coefficients from their highest level of decomposition are removed from the scaling function coefficients from the highest-level of decomposition of the prefiltered signal. Accordingly, a least squares fit between the interpolation points of the original signal and the reconstructed signal is calculated.

At step 222 compounds and concentrations present in the interrogated object are identified. The vector of amounts of each element found at step 220 is compared to the relative amounts of the elements stored to the algorithm at step 210 (or the subspaces formed by pairs of substances). Then, the angle between the vector of elements and each of the stored entries (or the subspaces formed by pairs) is calculated. The substance(s) that forms the smallest angle with our results vector is the best guess out of the substance library for the interrogated object that generated the spectral data. Applications that only want to identify the presence of elements in the spectral data without identifying the specific substance would forego this last portion of step 226.

In some embodiments of the algorithm, such as, for example, embodiments where user-defined levels of decomposition are not defined, additional steps may occur between step 220 (Calculate Least Squares Fit) and step 222 (Identify Compounds and Concentrations). Namely, an underlying curve may be calculated and a new best fit may be found based on the underlying curve. In calculating the underlying curve the interpolation points of the least squares fit calculated in step 220 minus the elements is used to construct a polynomial of degree 2 or less that is always below these points. The polynomial may have other features that may dictated by the algorithm (always decreasing, no inflection points, etc.). This polynomial is the so-called "underlying curve" from the background noise.

In finding a new best fit based on the underlying curve the amount of each element previously found is removed. The scaling function coefficients from the underlying curve plus a linear combination of the scaling function coefficients for each element being searched is combined with the same linear combination of the wavelet decompositions for each element, and the signal is once again reconstructed, thereby creating a "second reconstructed signal." The coefficients of the elemental wavelet decompositions are then solved for. Namely, coefficients are solved for that minimize the sum of the squares of the differences between the interpolation points of the curve from the second reconstructed signal and the interpolation values of the representative curve of the prefiltered data (the original signal). Again, the steps of calculating an underlying curve and finding a new best fit based on the underlying curve may be omitted when levels of decomposition are defined in step 210.

FIG. 7 provides an overview of the steps of an embodiment of the algorithm. The following description provides additional detail concerning an embodiment of the algorithm and includes sample programming code that may be utilized to implement the algorithm on an apparatus such as, for example, a computer. The system and method of embodiments of the present invention may be implemented using orthogonal multiwavelets as described through the following process.

The algorithm described in the following description is designed to analyze spectral data from a test material and detect the signatures associated with elements of the test material. The algorithm may also test for the presence of base elements or substances in the tested material. The algorithm takes advantage of one of the basic strengths of wavelets. Namely, that wavelet decompositions are not affected by background noise that is polynomial in nature up to the approximation order of the basis.

The steps of an embodiment of the algorithm will be described in detail hereinafter, along with programming that may be used to implement the algorithm. The programming is described in conjunction with a software package and language called Mathematica™, made by Wolfram Research. The Mathematica™ language is useful for describing the algorithm because it has several built-in commands that do not have to be programmed from scratch.

The Basis being Implemented

The algorithm uses an orthogonal, differentiable scaling vector of multiplicity-4 and approximation order 4. The scaling vector is an extension of a nonorthogonal scaling vector whose integer translates span the spline space $S_3^1$. The matrix coefficients of the scaling vector $\Phi=(\phi_1,\phi_2,\phi_3,\phi_4)^T$ satisfying the dilation equation $$\Phi(x) = \sqrt{2} \sum_{i=-2}^{1} g_i \Phi(2x - i)$$

are given below.

$$g_{-2} = \begin{bmatrix} 0 & 0 & 0.02669163201881291 & 0.026188780570349884 \\ 0 & 0 & -0.03940748766209954 & -0.040769035522339014 \\ 0 & 0 & 0 & 0 \\ 0 & 0 & 0 & 0 \end{bmatrix}$$

$$g_{-1} = \begin{bmatrix} -0.1175124743509559 & -0.10652668959666897 & 0.30676124077120465 & 0.35964167838854366 \\ 0.18731879383595215 & 0.18181954032277048 & -0.4224381824999862 & -0.433225475337907 \\ 0 & 0 & 0 & 0 \\ 0 & 0 & 0 & 0 \end{bmatrix}$$

$$g_0 = \begin{bmatrix} 0.7071067811865841 & 0 & 0.3067612407712861 & -0.3596416783882024 \\ 0 & 0.35355339059336993 & 0.42243818250022613 & -0.43322547533688205 \\ 0 & 0 & 0.47106586494422936 & 0.23604093395898632 \\ 0 & 0 & -0.5666158791523569 & -0.2916640296146426 \end{bmatrix}$$

$$g_1 = \begin{bmatrix} -0.11751247435904282 & 0.10652668958949803 & 0.0266916332347073 & -0.026188779541901065 \\ -0.1873187938600181 & 0.18181954030143205 & 0.03940749128037211 & -0.040769032461869345 \\ 0.6669057455800359 & 0 & 0.47106586494422936 & -0.23604093395898632 \\ 0 & 0.4333094490577162 & 0.5666158791523569 & -0.2916640296146426 \end{bmatrix}$$

Figure 8D:
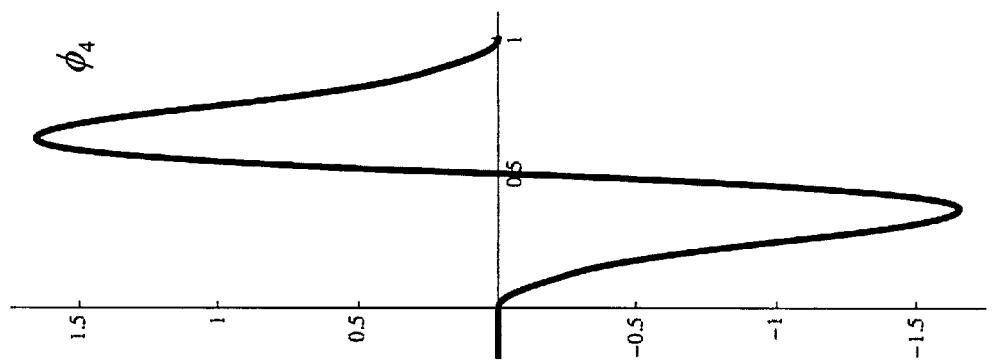
Figure 8C:
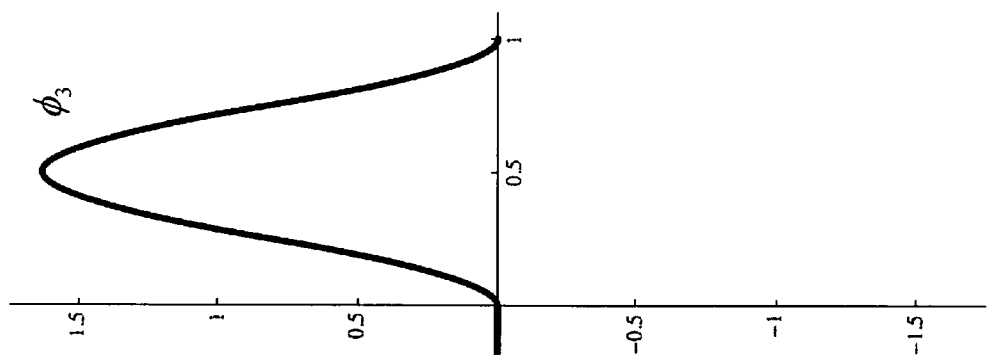

The individual elements of the orthogonal scaling vector $\phi$ are illustrated in FIGS. 8A through 8D. FIG. 8A illustrates $\phi_1$, FIG. 8B illustrates $\phi_2$, FIG. 8C illustrates $\phi_3$, and FIG. 8D illustrates $\phi_4$. The matrix coefficients are used to construct filters used to generate wavelet decompositions. The code in Mathematica™ for the filters for $\phi_1$, $\phi_2$, $\phi_3$, and $\phi_4$ is shown below.

```
cf1 = {0.026691562521021999630639608506914613,
    0.026188654278286972427140347852628382,
    -0.117512454242693769161095301758109618,
    -0.106526987474563491155721969664880935,
    0.306761317355368936258954257356829827,
    0.359641534154677908316734213716372821,
    0.707106781186547524400844362104849039,0,
    0.306761317355368936258954257356829827,
    -0.359641534154677908316734213716372821,
    -0.117512454242693769161095301758109618,
    -0.106526987474563491155721969664880935,
    0.026691562521021999630639608506914613,
    -0.026188654278286972427140347852628382};
```

```
cf2 = {-0.039407340780088115214335091368832779,
    -0.040768767875236487239820323387791847,
    0.187318711066355326125800356602148280,
    0.181820039817806532099999448762543406,
    -0.422438286949911730182156541480355150,
    -0.433225156682401886929031796408761180,0,
    0.353553390593273762200422181052424520,
    0.422438286949911730182156541480355150,
    -0.433225156682401886929031796408761180,
    -0.187318711066355326125800356602148280,
    0.181820039817806532099999448762543406,
    0.039407340780088115214335091368832779,
    -0.040768767875236487239820323387791847};
```

```
cf3 = {0.471065844835967531361517482810534138,
    0.236040936350579993039326879294314902,
    0.666905759752781871779187731727488879,0,
    0.471065844835967531361517482810534138,
    -0.236040936350579993039326879294314902};
```

```
cf4 = {-0.566615678874482047267309508338694444,
    -0.291663702551759245628871298813727359,0,
    0.433310413139146117896513537083926267,
    0.566615678874482047267309508338694444,
    -0.291663702551759245628871298813727359};
```

Also, the value of the functions at integer multiples of $$\frac{1}{4}$$

will be needed in this embodiment of the algorithm. The values are coded in below.

```
p1 = {0, 0.040346637381206616029156055501719646,
    -0.287638974096641942568520706848634016,
    0.537418274552907566890156181662808637,
    1.730807772061512250975665888026324598,
    0.537418274552907566890156181662808637,
    -0.287638974096641942568520706848634016,
    0.040346637381206616029156055501719646, 0};
```

```
p2 = {0, -0.049275988233777784095045031589808283,
    0.458505970515730986911530759287525803,
    -0.940707195821607327642760669284219140, 0,
    0.940707195821607327642760669284219140,
    -0.458505970515730986911530759287525803,
    0.049275988233777784095045031589808283, 0};
```

```
p3 = {0, 0.816203226248074372686601883825429452,
    1.632406452496148745373203767650858905,
    0.816203226248074372686601883825429452,0};
```

```
p4 = {0, -1.027103258082954429247792009842296911, 0,
    1.027103258082954429247792009842296911, 0};
```

All of the components are orthogonal to the integer translates of themselves and the other components. However, the restrictions of $\phi_1$ and $\phi_2$ to [0, 1], denoted $\phi_1|_{[0,1]}$ and $\phi_2|_{[0,1]}$, respectively, are not orthogonal, so in order to form scaling vector elements for a left boundary, it is necessary to project one out of the other. The two left-boundary functions $\phi_1^L$ and $\phi_2^L$ are defined by $$\phi_1^L = \frac{\phi_1|_{[0,1]} - \frac{\langle \phi_1|_{[0,1]}, \phi_2|_{[0,1]} \rangle}{\langle \phi_2|_{[0,1]}, \phi_2|_{[0,1]} \rangle} \phi_2|_{[0,1]}}{\left\| \phi_1|_{[0,1]} - \frac{\langle \phi_1|_{[0,1]}, \phi_2|_{[0,1]} \rangle}{\langle \phi_2|_{[0,1]}, \phi_2|_{[0,1]} \rangle} \phi_2|_{[0,1]} \right\|} \text{ and } \phi_2^L = \sqrt{2}\, \phi_2|_{[0,1]}.$$

The dilation equation for these two functions, $$\begin{bmatrix} \phi_1^L \\ \phi_2^L \end{bmatrix}(x) = g_0^L \begin{bmatrix} \phi_1^L \\ \phi_2^L \\ \phi_3 \\ \phi_4 \end{bmatrix}(2x) + g_1^L \Phi(2x-1),$$

is satisfied by the matrix coefficients $$g_0^L = \begin{bmatrix} 0.7071067811865475 & 0.6454740363938819 & -0.1876358734052539 & 0.0598156094040854 \\ 0 & 0.3535533905932737 & 0.5974179546702224 & 0.6126728921414618 \end{bmatrix}$$

and $$g_1^L = \begin{bmatrix} 0.1376997193243166 & -0.1558421660715024 & -0.0231700001401504 & 0.0281655443779667 \\ -0.2649086616762869 & 0.2571323662215582 & 0.0557303957882590 & -0.0576557444504000 \end{bmatrix}$$

The functions $\phi_1^L$, $\phi_2^L$, $\phi_1^R$, and $\phi_2^R$ are illustrated in respective of FIGS. 9A-9D.

Again, the matrix coefficients are used to construct filters used to generate wavelet decompositions. The necessary code in Mathematica™ for the filters for $\phi_1^L$ and $\phi_2^L$ is shown below.

cf1l = {0.70710678118654752440084436210484039,
0.64547403639388186483773975187472746,
-0.18763587340525389298917476901606355,
0.05981560940408537807752306195635677,
0.13769971932431663796833249001987180,
-0.15584216607150240330641017779200953,
-0.02317000014015036296852694474402989,
0.02816554437796674234821537533076963};

cf2l = {0, 0.35355339059327376220042218105242420,
0.59741795467022241681176961325881363,
-0.61267289214461836203967273925831971,
-0.26490866167628686776481105249254692,
0.25713236622155816341695707573836966,
0.05573039578825895582262297657091999,
-0.05765574445039998965178992450183282};

p1l = {5.0952193176012376369496633142453623470,
−0.84509212358976291501133793759608828,
0.33705198529886511113316974456842326,
−0.00845148185546189339863517137296173, 0};

p2l = {0, 1.32946076122292641253864185734531198,
−0.64842536193238520347936359782670720,
0.06968677085879910571404104375088487, 0};

Likewise, the two right-boundary functions $\phi_1^R$ and $\phi_2^R$ are defined by $$\phi_1^R(x) = \phi_1^R(1-x) \text{ and } \phi_2^R = -\phi_2^L(1-x).$$

The dilation equation for these two functions, $$\begin{bmatrix} \phi_1^R \\ \phi_2^R \end{bmatrix}(x) = g_0^R \Phi(2x) = g_1^R \Phi(2x-1) + g_2^R \begin{bmatrix} \phi_1^R \\ \phi_2^R \end{bmatrix}(2x-1),$$

is satisfied by the matrix coefficients $$g_0^R = \begin{bmatrix} 0 & 0 & -0.023100001401504 & -0.0281655443779667 \\ 0 & 0 & -0.0557303957882590 & -0.0576557444504000 \end{bmatrix},$$

$$g_1^R = \begin{bmatrix} 0.1376997193243166 & 0.1558421660715024 & -0.18763587340525390 & -0.0598156094040854 \\ 0.2649086616762869 & 0.2571323662215582 & -0.5974179546702224 & -0.6126728921414618 \end{bmatrix}$$

and $$g_2^R = \begin{bmatrix} 0.7071067811865475 & -0.6454740363938819 \\ 0 & 0.3535533905932738 \end{bmatrix}.$$

Also, the value of the functions at integer multiples of $$\frac{1}{4}$$

will be needed in this embodiment of the algorithm. The necessary code in Mathematica™ to code the values is shown below.

Figure 9A:
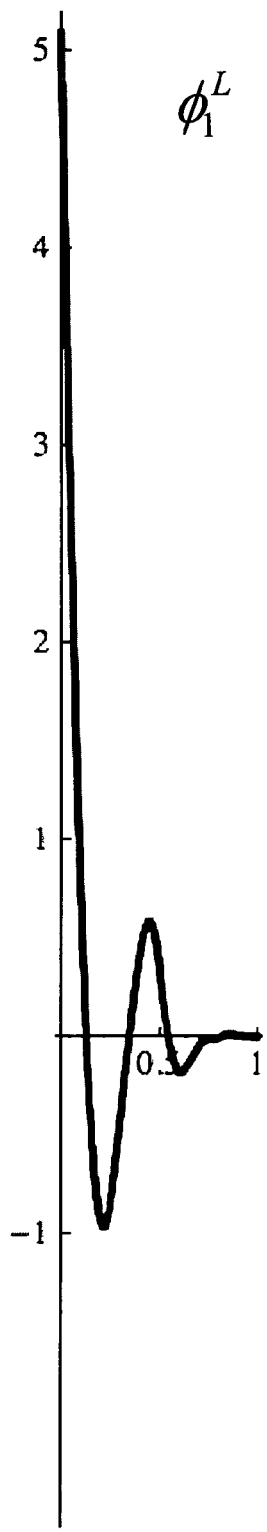
FIGS. 9A through 9D illustrate boundary functions $\phi_1^L$, $\phi_2^L$, $\phi_1^R$, and $\phi_2^R$, respectively.
Figure 9B:
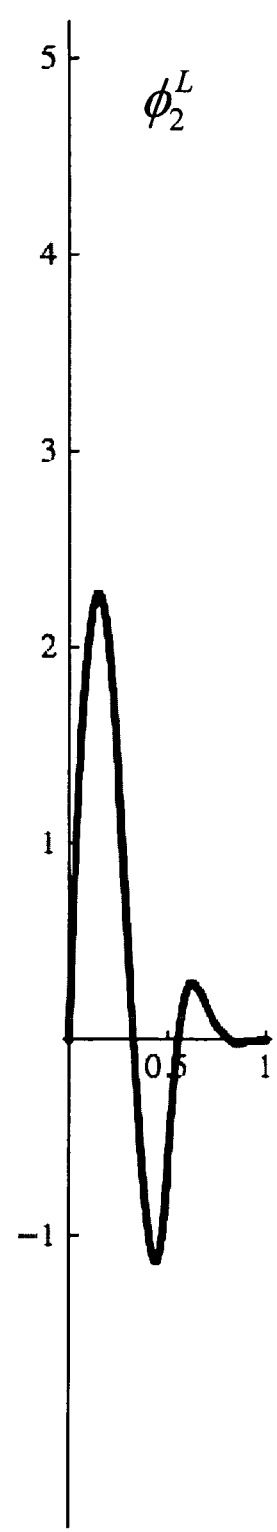
Figure 9C:
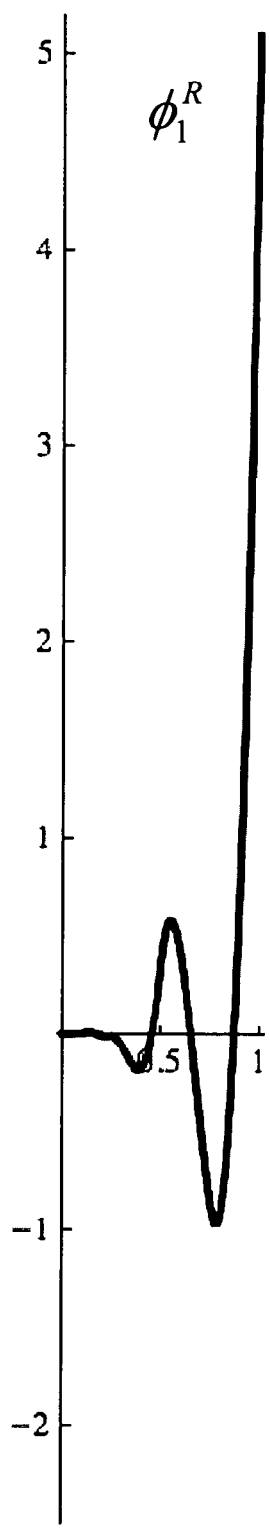
Figure 9D:
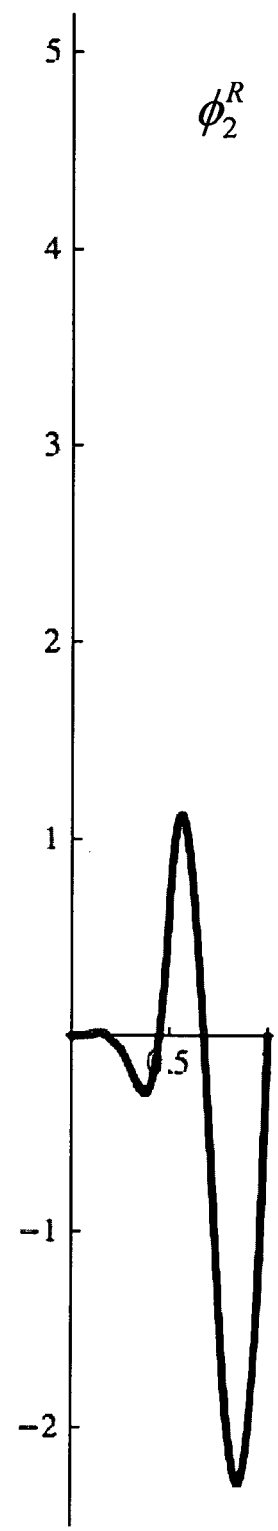

The functions are also illustrated in FIGS. 9C($\phi_1^R$) and 9D($\phi_2^R$).

Again, the matrix coefficients are used to construct filters used to generate wavelet decompositions. The code in Mathematica™ for the filters for $\phi_1^R$ and $\phi_2^R$ is shown below.

$cf1r = \{-0.023170000140150362968526944744029897,$
$-0.028165544377966742348215375220769636,$
$0.137699719324316637968332490019871801,$
$0.155842166071502403306471017792009533,$
$-0.187635873405253892989174769016063955,$
$-0.059815609404085378077523061956355677,$
$0.707106781186547524400844362104849039,$
$-0.645474036393881864837739751874727746\};$ $cf2r = \{-0.055730395788258955822622976570919991,$
$-0.057655744450399989651789924501832829,$
$0.264908661686286867764811052492546928,$
$0.257132366221558163416957075738369662,$
$-0.597417954670222416811769613258813637,$
$-0.612672892141461836203967273925831971, 0,$
$0.353553390593273762200422181052424520\};$ $p1r = \{0, -0.008451481855461893398635171372961730,$
$0.337051985298865111331697445684232671,$
$-0.845092123589762915011337937596088281,$
$5.095219317601237636949663314245362347\};$ $p2r = \{0, -0.069867708589799105714041043750884 87,$
$0.648425361932385203479363597826707207,$
$-1.329460761222926412538641857345311981, 0\};$

The Associated Multiwavelets

The matrix coefficients of the multiwavelet $\Psi=(\psi_1, \psi_2, \psi_3, \psi_4)^T$ satisfying the dilation equation $$\Psi(x) = \sqrt{2} \sum_{i=-2}^{1} h_i \Phi(2x - i)$$

are shown below.

$$h_{-2} = \begin{bmatrix} 0 & 0 & 0.0266916313500821 & 0.02618877991421749 \\ 0 & 0 & 0.04374365300600389 & 0.06435982959198171 \\ 0 & 0 & -0.013410540810749855 & -0.013157895717088848 \\ 0 & 0 & -0.04006995259666773 & -0.06065185761803572 \end{bmatrix}$$

$$h_{-1} = \begin{bmatrix} -0.117751247140680435 & -0.10652668692775463 & 0.3067612330856239 & 0.3596416693780991 \\ -0.3334538093583893 & -0.424692849463 17537 & 0.19229779050087667 & -0.40670678109361624 \\ 0.05904119433180234 & 0.053521662417019424 & -0.15412448873935367 & -0.18069293784197155 \\ 0.3166000901995356 & 0.40882389594960616 & -0.15157506646288127 & 0.4513983241700974 \end{bmatrix}$$

$$h_0 = \begin{bmatrix} -0.7071067870918081 & 0 & 0.30676123308570535 & -0.3596416693777578 \\ 0 & 0 & 0.19229779050222978 & 0.40670678109948577 \\ 0 & -0.9347644627208598 & 0.15412448873939458 & -0.18069293784180007 \\ 0 & -0.034862829700229456 & 0.15157506646421717 & 0.45139832417589415 \end{bmatrix}$$

$$h_1 = \begin{bmatrix} -0.11751247141489118 & 0.10652668692058369 & 0.02669163256597651 & -0.026188778885768697 \\ -0.3334538094952175 & 0.424692849341863 & 0.043743673577174123 & -0.06435981219212034 \\ -0.05904119433586537 & 0.05352166241341656 & 0.013410541421645506 & -0.013157895200370542 \\ -0.31660009033465436 & 0.40882389582980966 & 0.04006997291081938 & -0.060651840435570266 \end{bmatrix}$$

Also, the value of the functions at integer multiples o $$\frac{1}{4}$$

willf be needed in embodiments of the algorithm. The Mathematica™ values are shown below.

Figures 10A, 10B:
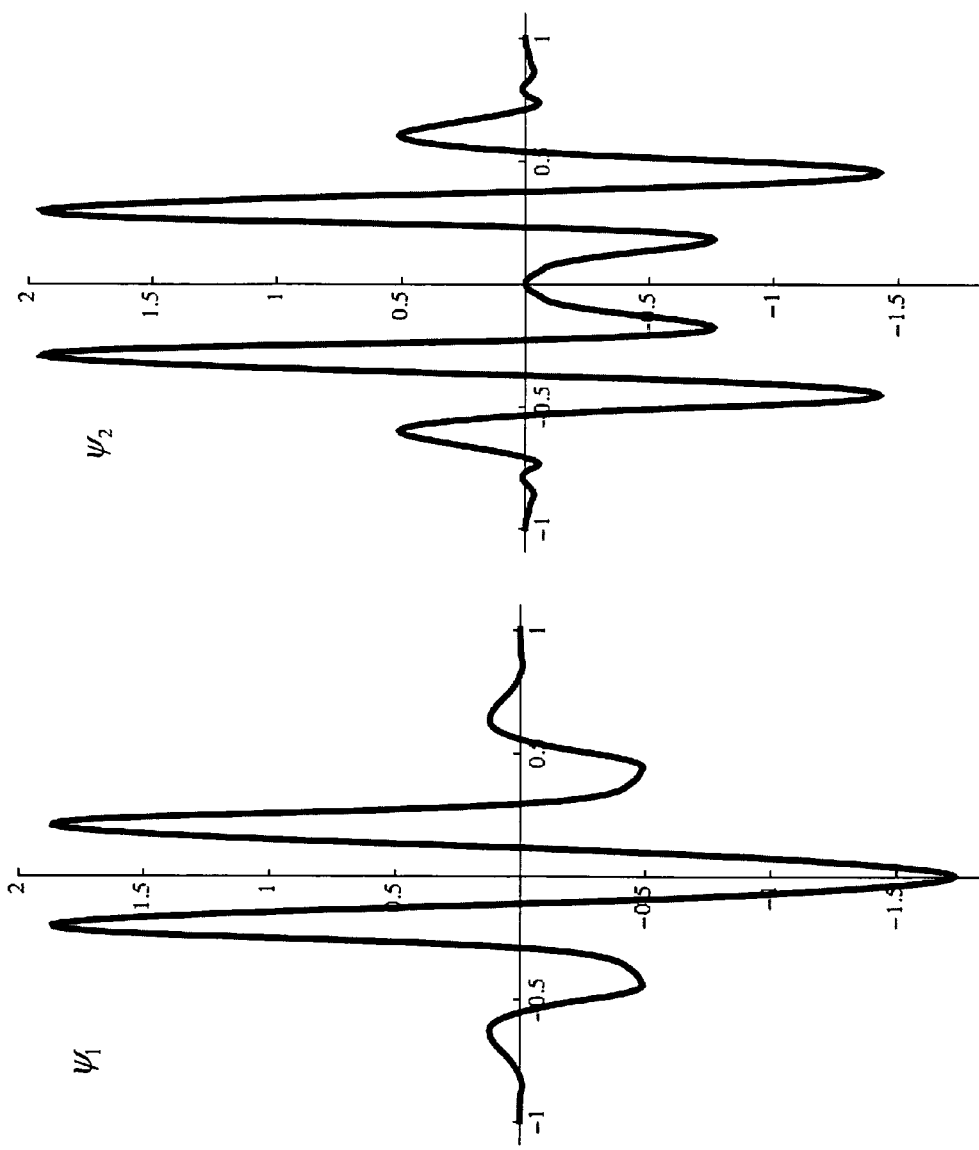
FIGS. 10A through 10D illustrate the multiwavelet $\Psi$.
Figure 10D:
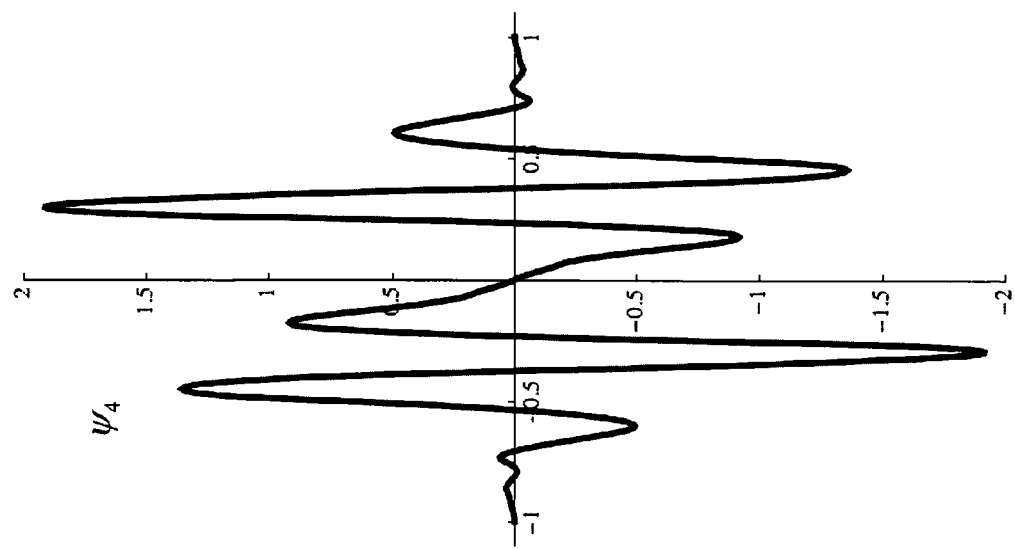
Figure 10C:
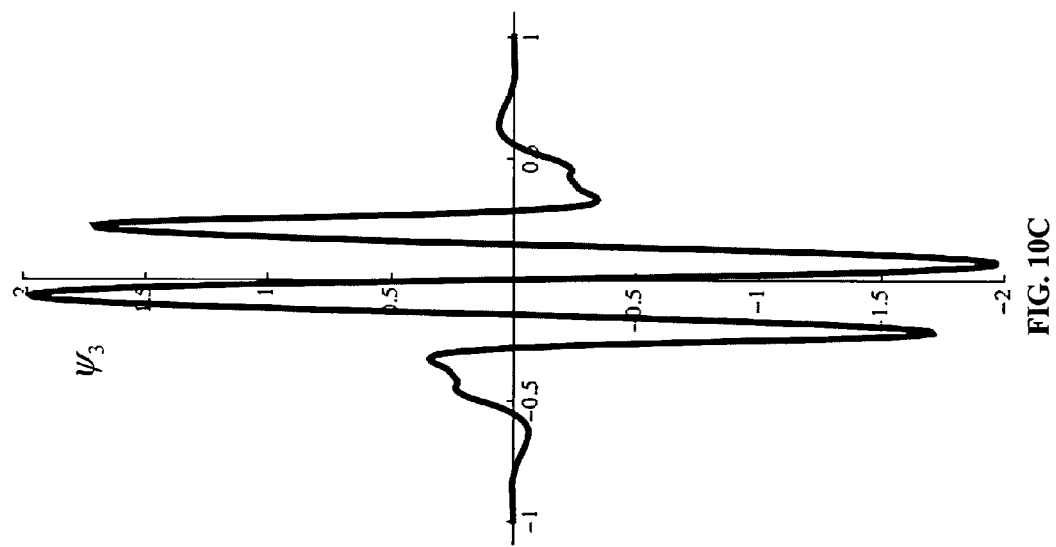
Figure 11A:
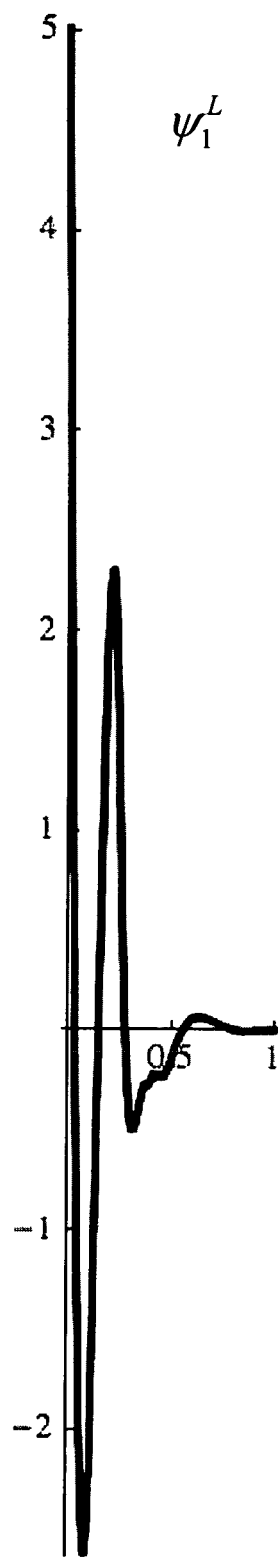
Figure 11B:
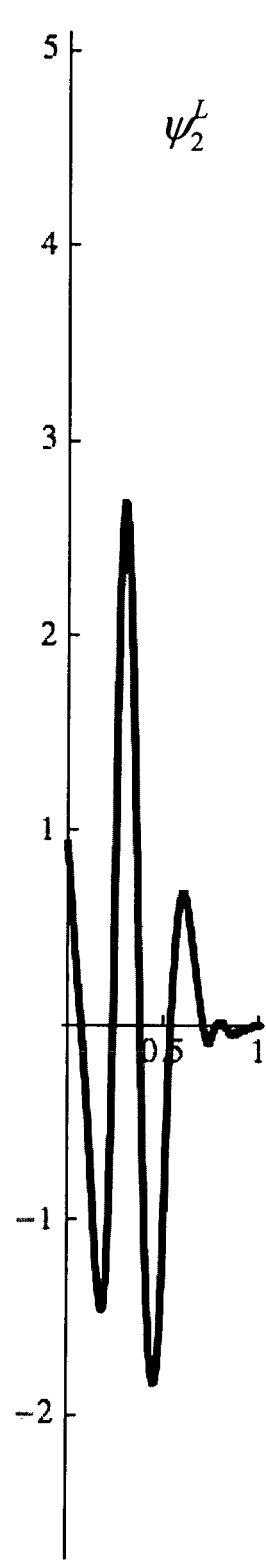

The individual elements of the multiwavelet are illustrated in FIGS. 10A-D. FIG. 10A illustrates $\psi_1$, FIG. 10B illustrates $\psi_2$, FIG. 10C illustrates $\psi_3$, and FIG. 10D illustrates $\psi_4$.

The matrix coefficients are used to construct filters used to generate wavelet decompositions. The code in Mathematica™ for the filters for $\psi_1, \psi_2, \psi_3,$ and $\psi_4$ is shown below.

$w1 = \{0.026691562521021999630639608506914614,$
$0.026188654278286972427140347852628382,$
$-0.117512454242693769161095301758109621,$
$-0.106526987474563491155721969664880938,$
$0.306761317355368936258954257356829834,$
$0.359641534154677908316934213716372830,$
$-0.707106781186547524400844362104849034, 0,$
$0.306761317355368936258954257356829834,$
$-0.359641534154677908316734213716372830,$
$-0.117512454242693769161095301758109621,$
$0.106526987474563491155721969664880938,$
$0.026691562521021999630639608506914614,$
$-0.026188654278286972427140347852628382\};$ $w2 = \{0.043743053526442261379028944519498646,$
$0.064358730437004537811610431129711934,$
$-0.333452879876390935889593865863744458,$
$-0.424693446318028332458623851693453403,$
$0.192297882824137731660297934774816291,$
$-0.406707114398962993549907051680822183,$
$0, 0, 0.192297882824137731660297934774816291,$
$0.406707114398962993549907051680822183,$
$-0.333452879876390935889593865863744458,$
$0.424693446318028332458623851693453403,$
$0.043743053526442261379028944519498646,$
$-0.064358730437004537811610431129711934\};$ $w3 = \{-0.013410507262869283565291187604616349,$
$-0.013157833608547128185413343932297134,$
$0.059041190258459963412084188561761797,$
$0.053521817544180235580085768787030359,$
$-0.154124542957030643706932521769576038,$
$-0.180692883828447055457637053306489521, 0,$
$-0.934764451186885779186744765104492524,$
$0.154124542957030643706932521769576038,$
$-0.180692883828447055457637053306489521,$
$-0.059041190258459963412084188561761797,$
$0.053521817544180235580085768787030359,$
$0.013410507262869283565291187604616349,$
$-0.013157833608547128185413343932297134\};$ $w4 = \{0.040069359104420172186166185312101487,$
$-0.060650774025919606993540520908232495,$
$0.316599139669464073271883224610855942,$
$0.408824423969586170784948965635551698,$
$-0.151575084914899545346374620669748655,$
$0.451339870229350411456606571454105924, 0,$
$-0.034862885670584318437515767031413216,$
$0.151575084914899545346374620669748655,$
$0.451339870229350411456606571454105924,$
$-0.316599139669464073271883224610855942,$
$0.408824423969586170784948965635551698,$
$0.040069359104420172186166185312101487,$
$-0.060650774025919606993540520908232495\};$

Multiwavelet components for the boundaries are used as well. The dilation equation for the two left-boundary functions, $$\begin{bmatrix} \psi_1^L \\ \psi_2^L \end{bmatrix}(x) = h_0^L \begin{bmatrix} \phi_1^L \\ \phi_2^L \\ \phi_3 \\ \phi_4 \end{bmatrix}(2x) + h_1^L \Phi(2x-1),$$

is satisfied by the matrix coefficients $$h_0^L = \begin{bmatrix} 0.6951638621828865 & -0.6719566495139803 & 0.1566844392244006 & -0.1836940608634487 \\ 0.1294109914766624 & 0.0826893555140895 & 0.1835797585076520 & 0.6599242367667018 \end{bmatrix} \text{ and}$$

$$h_1^L = \begin{bmatrix} -0.0600218213744650 & 0.0544107759042540 & 0.0136332460092565 & -0.0133763756297915 \\ -0.4299743283383988 & 0.5592465251689393 & 0.0533673700394672 & -0.0820430657358089 \end{bmatrix}$$

The dilation equation for the two right-boundary functions, $$\begin{bmatrix} \psi_1^R \\ \psi_2^R \end{bmatrix}(x) = h_0^R \Phi(2x) + h_1^R \Phi(2x-1) + h_2^R \begin{bmatrix} \phi_1^R \\ \phi_2^R \end{bmatrix}(2x-1), \qquad 5$$

is satisfied by the matrix coefficients $$h_0^R = \begin{bmatrix} 0 & 0 & 0.0136332460092565 & 0.0133763756297915 \\ 0 & 0 & -0.0533673700394672 & -0.0820430657358089 \end{bmatrix},$$

$$h_1^R = \begin{bmatrix} -0.0600218213744650 & -0.0544107759042540 & 0.1566844392244006 & 0.1836940608634487 \\ 0.4299743283383988 & 0.5592465251689393 & -0.1835797585076520 & 0.6599242367667018 \end{bmatrix}, \text{ and}$$

$$h_2^R = \begin{bmatrix} 0.6951638621828865 & 0.6719566495139803 \\ -0.1294109914766624 & 0.0826893555140895 \end{bmatrix}.$$

The boundary functions $\psi_1^L$, $\psi_2^L$, $\psi_1^R$, and $\psi_2^R$ are illustrated in respective of FIGS. 11A-D.

Again, the matrix coefficients are used to construct filters used to generate wavelet decompositions. The code in Mathematica™ for the filters for $\psi_1^L$, $\psi_2^L$, $\psi_1^R$, and $\psi_2^R$ is shown below.

$$w1l = \{0.6951638621828864929793783660232165 69,$$
$$-0.6719566495139803219990573293370430 39,$$
$$0.1566844392244006373044361020446896 05,$$
$$-0.1836940608634486784056427273990576 14,$$
$$-0.0600218213744649618872969196247725 44,$$
$$0.0544107759042540285707222789278159 74,$$
$$0.0136332460092565361723472572759046 90,$$
$$-0.0133763756297915049288593680784633 19\};$$

$$w2l = \{0.1294109914766624235378290322529461 62,$$
$$0.0826893555140894717554243003773986 32,$$
$$0.1835797585076519858431742149873687 64,$$
$$0.6599242367667018379198233572572118 04,$$
$$-0.4299743283383988438947522405814027 28,$$
$$0.5592465251689393040493204929154240 33,$$
$$0.0533673700394672061157984923795214 81,$$
$$-0.0820430657358088949884123586699738 22\};$$

$$w1r = \{0.0136332460092565361723472572759046 90,$$
$$0.0133763756297915049288593680784633 19,$$
$$-0.0600218213744649618872969196247725 44,$$
$$-0.0544107759042540285707222789278159 74,$$
$$0.1566844392244006373044361020446896 05,$$
$$0.1836940608634486784056427273990576 14,$$
$$0.6951638621828864929793783660232165 69,$$
$$0.6719566495139803219990573293370430 39\};$$

-continued $$w2r = \{-0.0533673700394672061157984923795214 81,$$
$$-0.0820430657358088949884123586699738 22,$$
$$0.4299743283383988438947522405814027 28,$$
$$0.5592465251689393040493204929154240 33,$$
$$-0.1835797585076519858431742149873687 64,$$
$$0.6599242367667018379198233572572118 04,$$
$$-0.1294109914766624235378290322529461 62,$$
$$0.0826893555140894717554243003773986 32\};$$

The Prefilter being Implemented

When applying multiwavelets, it is necessary to prefilter the data in order to maintain its polynomial order. Prefiltering is the process of turning the raw data into basis coefficients, and is usually achieved by convolving matrix filters over the data. The most easily applied order-preserving prefilter is the interpolation filter, mapping the raw data to the basis elements that will form a curve that interpolates the data. However, such an interpolation prefilter is not the most advantageous for this basis. As previously discussed, embodiments of the algorithm use a quasi-interpolation filter that preserves approximation order up through degree-3 (cubic) polynomials, the approximation order of the basis, applied to three consecutive 4-vectors of data, $$Q_1 \begin{bmatrix} y_0 \\ y_1 \\ y_2 \\ y_3 \end{bmatrix} + Q_2 \begin{bmatrix} y_4 \\ y_5 \\ y_6 \\ y_7 \end{bmatrix} + Q_3 \begin{bmatrix} y_8 \\ y_9 \\ y_{10} \\ y_{11} \end{bmatrix}, \text{ where}$$

$$Q_1 = \begin{bmatrix} 0 & 0 & -0.0361103054577686 & 0.14444122183120744 \\ 0 & 0 & 0.0143891218163777 & -0.1151129745310218 \\ 0 & 0 & 0 & 0 \\ 0 & 0 & 0 & 0 \end{bmatrix},$$

$$Q_2 = \begin{bmatrix} 0.361103054577686 & 0.1444412218310744 & -0.036110305477686 & 0 \\ 0 & 0.1151129745310218 & -0.0143891218163777 & 0 \\ 0.0022936998896412 & 0.2040508104236080 & 0.4035142210679336 & 0.2040508104236080 \\ 0.0025313537751359 & -0.2871336777193043 & 0 & 0.2871336777193043 \end{bmatrix}, \text{ and}$$

$$Q_3 = \begin{bmatrix} 0 & 0 & 0 & 0 \\ 0 & 0 & 0 & 0 \\ 0.0022936998896412 & 0 & 0 & 0 \\ -0.0025313537751359 & 0 & 0 & 0 \end{bmatrix}.$$

On the left boundary, the following filter is used with the same properties, $$Q_1^L \begin{bmatrix} y_0 \\ y_1 \\ y_2 \\ y_3 \end{bmatrix} + Q_2^L \begin{bmatrix} y_4 \\ y_5 \\ y_6 \\ y_7 \end{bmatrix}, \text{ where}$$

$$Q_1^L = \begin{bmatrix} 0.1962623971750690 & 0 & 0 & 0 \\ 0.1344693983193775 & 0.3662872420204795 & -0.1831436210102398 & 0.0406985824467199 \\ 0 & 0.2132256099821730 & 0.3897520217300861 & 0.2132256099821730 \\ 0.0025313537751359 & -0.2871336777193043 & 0 & 0.2871336777193043 \end{bmatrix} \text{ and}$$

$$Q_2^L = \begin{bmatrix} 0 & 0 & 0 & 0 \\ 0 & 0 & 0 & 0 \\ 0 & 0 & 0 & 0 \\ -0.0025313537751359 & 0 & 0 & 0 \end{bmatrix}.$$

On the right boundary, the data is padded with three 0's and the following filter is used, $$Q_1^R \begin{bmatrix} y_0 \\ y_1 \\ y_2 \\ y_3 \end{bmatrix} + Q_2^R \begin{bmatrix} y_4 \\ 0 \\ 0 \\ 0 \end{bmatrix}, \text{ where}$$

$$Q_1^R = \begin{bmatrix} 0 & 0 & 0 & 0 \\ 0 & -0.0406985824467199 & 0.1831436210102398 & -0.3662872420204795 \\ 0 & 0 & 0 & 0 \\ 0 & 0 & 0 & 0 \end{bmatrix} \text{ and}$$

$$Q_2^R = \begin{bmatrix} 0.1962623971750690 & 0 & 0 & 0 \\ -0.1344693983193776 & 0 & 0 & 0 \\ 0 & 0 & 0 & 0 \\ 0 & 0 & 0 & 0 \end{bmatrix}.$$

In Mathematica™, the code for the prefilters is shown below.

$Q1 = \{\{0, 0, -0.036110306995882136432457014822783018,$
$0.144441227983528548729828059291132071\}, \{0,0,$
$0.0143891251127462120131100747870 82622,$
$-0.115113000901969696104880598296660973\}, \{0, 0, 0, 0\},$
$\{0, 0, 0, 0\}\};$ $Q2 = \{\{0.36110306995882136432457014 8227830177,$
$0.144441227983528548729828059291132071,$
$-0.036110306995882136432457014822783018, 0\}, \{0,$
$0.115113000901969696104880598296660973,$
$-0.0143891251127462120131100747870 82622, 0\},$
$\{0.002293697086602093003612981907273363,$
$0.204050806562018593171650470956357363,$
$0.403514218950833000336074978098168000,$
$0.204050806562018593171650470956357363\},$
$\{0.002531342478553625493883391236995688,$
$-0.287133633597856218574804478062066924, 0,$
$0.287133633597856218574804478062066924\}\};$ $Q3 = \{\{0, 0, 0, 0\}, \{0, 0, 0, 0\},$
$\{0.002293697086602093003612981907273363,0,0,0\},$
$\{-0.002531342478553625493883391236995688,0,0,0\}\};$ $Qlt1 = \{\{0.196262405534839052164430480811468970,0,0,0\},$
$\{0.134469362302152422735354388972236150,$
$-0.183143662966160850862991180697365022,$
$0.040698591770257966858442484599414449\}, \{0,$
$0.213225594908426965186102398585450816,$
$0.389752036431220442314397086654527821,$
$0.213225594908426965186102398585450816\},$
$\{0.002531342478553625493883391236995688,$
$-0.287133633597856218574804478062066924,0,$
$0.287133633597856218574804478062066924\}\};$ $Qlt2 = \{\{0, 0, 0, 0\}, \{0, 0, 0, 0\}, \{0, 0, 0, 0\},$
$\{-0.002531342478553625493883391236995688, 0, 0, 0\}\};$ $Qrt1 = \{\{0, 0, 0, 0\}, \{0,$
$-0.040698591770257966858442484599414449,$
$0.183143662966160850862991180697365022,$
$-0.366287325932321701725982361394730044\}, \{0, 0, 0, 0\},$
$\{0, 0, 0, 0\}\};$ $Qrt2 = \{\{0.196262405534839052164430480811468970,0,0,0\},$
$\{-0.134469362302152422735354388972236150,0,0,0\},$
$\{0, 0, 0, 0\}, \{0, 0, 0, 0\}\};$

This quasi-interpolation prefilter is not orthogonal (that is, it does not preserve the norm of the original data), and it is not invertible. Therefore, when comparisons of wavelet decompositions occur they will not be compared directly. Rather, the signal will be reconstructed and postfiltered with the inverse of the interpolation prefilter, and interpolation points are compared along the approximation of the original from the quasi-interpolation prefilter and the reconstructed curves.

Preliminary Inputs into the Algorithm

As described with respect to step 210 of FIG. 7, some information needs to be entered prior to actually implementing the algorithm. The amount of information is dependent on the specific elements that will be searched and the specific compounds, if any, that will be searched.

Information about the elements to be searched needs to be input into the algorithm before the actual analysis of the data. For example, for each element, one or more of the following aspects of elemental data is needed: the location of the Gaussian peaks, the relative heights of the Gaussian peaks, and the standard deviation (or equivalently, the full-width at half maximum) of the Gaussian peaks. A search threshold and decomposition level also need to be entered into the algorithm in order to fine-tune the location of the peaks in the data. The search threshold may be dependent on the perceived accuracy of the calibration of the device collecting the data (e.g., a gamma ray detector) and/or the proximity of the peaks for the elements that are being searched. The level of decomposition may be dependent upon the curvature of the underlying background distortion of the data.

The locations and relative heights are theoretical values associated with elements, while the standard deviations of each peak will be dependent on the detector that is being used. From this information, a curve can be built to represent each element. An element having k peaks at $x=x_1^*, \ldots, x_k^*$ with relative heights $m_1, \ldots, m_k$ and standard deviations $\sigma_1, \ldots, \sigma_k$, respectively, can be represented by the formula $$\sum_{i=1}^{k} m_i e^{-\frac{(x-x_i^*)^2}{2\sigma_i^2}}.$$

The $x_i$ for each element can be arranged from least to greatest. For each element, two values may be calculated, $$\min = x_1 - 3\sigma_1 \text{ and } \max = x_k + 3\sigma_k.$$

The minimum of all the min's will be denoted herein as $\alpha$, and the maximum of all of the max's we will denoted herein as $\omega$. All of our analysis will take place over the interval $[\alpha, \omega]$. The values for $\alpha$ and $\omega$ may be reset after adjustment of the peak locations of the elements occurs. The accuracy of the algorithm is improved if all elements that have Gaussian peaks that overlap the analysis window $[\alpha, \omega]$ are also included in the element library, although those elements will not alter the size of the analysis window.

Compounds Information

As described with respect to step 222 of FIG. 7, the algorithm may identify specific compounds if desired. This section of the algorithm is optional, as some applications may only want to identify the presence of elements. However, if the goal is to identify compounds in the test material, then a library of these compounds should be inputted before implementing the algorithm as described with respect to step 210. For example, assume an ordering on the elements for which a search is conducted. For each compound to identify, associate a vector of that length that gives the relative amounts of each element in that compound. For example, if we are searching on carbon, hydrogen, nitrogen, and oxygen, then we could assume that ordering and use the 4-vector (0, 2, 0, 1) to represent water ($H_2O$).

The only restriction on the library is that different compounds that have the same vector when restricted to the search elements should not be included. In mathematical terms, all of the vectors should be linearly independent. If two compounds have the same vector of elements, then it may be accepted that the two compounds are indistinguishable by the algorithm, or a search on more elements may occur so that the vectors for the two compounds are different.

The Algorithm

The following sections illustrate the steps of the algorithm, which may be implemented on an exemplary system, and show pertinent Mathematica™ code used to implement the steps. In some embodiments one or more steps of the algorithm may be implemented on an exemplary system utilizing a programming language other than Mathematica™ such as, for example, the C or C++ programming language.

Receive Raw Spectral Data and Perform Decompositions

As described with respect to steps 212, 214, and 216 of FIG. 7, the algorithm receives raw spectral data, prefilters the spectral data, and then decomposes the prefiltered data. Once the raw spectral data is read into memory, the number of data values that fall into the analysis window [α, ω] may be counted, said number of data values may be denoted as P herein. Next, a number N that denotes the maximum number of levels to which the data will be decomposed is determined, by setting $$N = \lfloor \log_2 P \rfloor - 2.$$

This will also determine the number of data points that we use in each of the decompositions, both for the elements and the data. Alternatively, a lower level of decompositions can be specified by the user by manually setting the level to be less than N.

For each of the two components of the scaling vector supported on [0, 1], and for the four boundary functions (two on each edge) that accompany the scaling vector, $2^{N+2}+1$ uniformly-sampled function values on [0, 1] can be calculated. The function values will assist in reconstructing curves represented by the vector of coefficients of the smoothest approximation at the highest level of decomposition. Sample Mathematica™ code is shown below.

phi[0]={1.7308078457850338, 0, 0, 0}//N;
phi[x_]:=If[x≦−1||x≧1, {0., 0., 0., 0.}, phi[x]];
phi[3]
{0., 0., 0., 0.}
fill[j_]:=Do[phi[x]=√2 Sum [G[i].phi[2x−i], {i, −2, 1}], {x, −1, 1, $2^{-j}$}];
fill[1]
fill[2]
fill[3]
fill[4]
fill[5]
Fill[6]
fill[7]
fill[8]
f12=0.87705074833199150864573857993286486711 4269913358;

$$pts1 = \frac{\sqrt{2}}{\sqrt{1-f12^2}} (\text{Table}[phi[x][[1]], \{x, 0, 2, 2^{-11}\}] - f12 * \text{Table}[phi[x][[2]], \{x, 0, 2, 2^{-11}\}]);$$

pts2=√2 Table[phi[x][[1]], {x, 0, 2, $2^{-11}$}];
pts3=Table[phi[x][[3]], {x, 0, 2, $2^{-11}$}];
pts4=Table[phi[x][[4]], {x, 0, 2, $2^{-11}$}];
pts5=Table[phi[x][[1]], 55 x, −1, 1, $2^{-11}$}];
pts6=Table[phi[x][[2]], {x, −1, 1, $2^{-11}$}];
pts7=Table[phi[x][[3]], {x, −1, 1, $2^{-11}$}];
pts8=Table[phi[x][[4]], {x, −1, 1, $2^{-11}$}];

$$pts9 = \frac{\sqrt{2}}{\sqrt{1-f12^2}} (\text{Table}[phi[x][[1]], \{x, -2, 0, , 2^{-11}\}] + f12 * \text{Table}[phi[x][[2]], \{x, -2, 0, 2^{-11}\}]);$$

pts10=√2 Table[phi[x][[2]], {x, −2, 0, $2^{-11}$}];

The raw data is fit with a cubic spline, and $2^{N+2}+1$ samples at uniform locations on the interval [α, ψ] are taken. Sample code in Mathematica™ with N=10 is shown below.
Clear[f1];
tmat=Transpose[temp];
Dimensions[tmat]
{2, 4096}
f1=ListInterpolation[tmat[[2]], {tmat[[1]]}]
InterpolatingFunction[{{−5.72511, 10048.6}}, "< >"]

$$\text{temp} = \text{Table}\left[\{x, f1[x]\}, \left\{x, \text{low, high}, \frac{\text{high}-\text{low}}{4096}\right\}\right];$$

$$\text{vals} = \text{Table}\left[f1[x], \left\{x, \text{low, high}, \frac{\text{high}-\text{low}}{4096}\right\}\right];$$

len=Length[vals]
4097

Herein, N* will denote the user-input level of decomposition inputted in the algorithm initialization and N* will be less than or equal to N. The smoother approximation at level N* is found, and subtracted from the original data, with negative values set to 0. Sample code in Mathematica™ with N*=9 is shown below.
c9
{793.0789417, 856.5248688, 638.8239578, −231.7022737, 196.8018374, −5.470671234, 185.1280008, −27.66322817, 26.34296641, −56.76951784}

$$\text{approx} = 2^{-\frac{9}{2}} (c9[[1]] * pts1 + c9[[2]] * pts2 + c9[[3]] * pts3 + c9[[4]] * pts4 + c9[[5]] * pts5 + c9[[6]] * pts6 + c9[[7]] * pts7 + c9[[8]] * pts8 + c9[[9]] * pts9 + c9[[10]] * pts10);$$

$$\text{adtemp} = \text{Table}[\{temp[[i, 1]] temp[[i, 2]] - approx[[i]], \{i, \text{Length}[temp]\}];$$

For each given peak location, adjusted data points within the user-defined threshold around each given peak location are collected. The number of data points that would fall within 6 standard deviations is calculated, and the sums of the adjusted data values over data intervals of that number are found. On the subinterval of the adjusted data with the maximum sum, the center of mass of that data is statistically calculated, and the peak location reset to that amount. In the event that all of the adjusted data values are zero, the peak location remains the user-input amount. Sample code in Mathematica™ is shown below.

```
carbcenter=4439; carbsd=3.5;
i=1;
While[temp[[i, 1]]<carbcenter-tol, i++];
lowpos=i-1;
While[temp[[i, 1]]<carbcenter+tol, i++];
highpos=i;
data=adtemp[[Range[lowpos, highpos]]];
data=Table[{data[[i, 1]], Max[data[[i, 2]], 0]}, {i, Length[data]}];

If[Max[Transpose[data][[2]]] > 0,
(
```

$$\text{rate} = \frac{\text{data}[[\text{Length}[\text{data}], 1]] - \text{data}[[1, 1]]}{\text{Length}[\text{data}] - 1};$$

$$\text{num} = \text{Ceiling}\left[\frac{3 * \text{barbsd}}{\text{rate}}\right];$$

$$\text{list} = \text{Table}\left[\text{Sum}\left[\text{data}[[i + k, 2]] * E^{-\frac{k^2}{2\left(\frac{\text{num}}{3}\right)^2}}, \{k, -\text{num}, \text{num}\}\right],\right.$$
$$\{i, 1 + \text{num}, \text{Length}[\text{data}] - \text{num}\}\Big];$$

$$\text{pos} = \text{Position}[\text{list}, \text{Max}[\text{list}]][[1, 1]];$$

$$\text{carbcenter} = \text{Sum}[\text{data}[[\text{pos} + \text{num} + k, 1]] *$$
$$\text{data}[[\text{pos} + \text{num} + k, 2]], \{k, -\text{num}, \text{num}\}]$$
$$\text{Sum}[\text{data}[[\text{pos} + \text{num} + k, 2]], \{k, -\text{num}, \text{num}\}];$$

)];

Print[carbcenter]
4403.079074
ht=NSolve[Integrate[k*E^(-(x^2/(2(carbsd)^2))),
    {x, -6 carbsd, 6 carbsd}]=100, k]
{{k→11.39835089}}

$$\text{carb}[x\_] := 0.5939556518961335 * ht[[1, 1, 2]] * E^{-\frac{(x-\text{carbcenter})^2}{2(\text{carbsd})^2}};$$

For each of the elements, sample the function representing the Gaussian peaks associated with that element at $2^{N+2}+1$ uniform locations along the analysis window [α, ω]; that is, sample the function at $x_i$, where $$x_i = \alpha + \frac{\omega - \alpha}{2^{N+2}}(i-1) \text{ for } i = 1, \ldots, 2^{N+2} + 1.$$

Sample code in Mathematica™ with N=10 and carbon (carb[x]) as the elemental peaks function, is shown below.

$$\text{temp} = \text{Table}\left[\text{carb}[x], \left\{x, \text{low}, \text{high}, \frac{\text{high}-\text{low}}{4096}\right\}\right];$$

len=Length[temp]
4097

The data is then "padded" with three zeroes, and the prefilter for the basis is applied. Sample code from Mathematica™ is shown below.

```
temppad=Join[temp, {0, 0, 0}]//Flatten;
c0=Join[Qlt1.temppad[[{1, 2, 3, 4}]]+Qlt2.temppad[[{5, 6, 7, 8}]]], Table[Q1.temppad[[Range[i, i+3]]]+Q2.temppad[[Range[i+4, i+7]]]+Q3.temppad[[Range[i+8, i+11]]], {i, 1, len-8, 4}], Qrt1.temppad[[Range[len-4, len-1]]]+Qrt2.temppad[[Range[len, len+3]]]]//Flatten//Simplify//Chop;
c0=c0[[Range[1, len+1]]];
```

The prefiltered signal $c_0$ is then decomposed using the filters for the basis. Sample code is shown below for the first-level decomposition into $c_1$ and $d_1$. The code for the decompositions at the other levels is analogous.

$$\text{lenold} = \text{Length}[c0]; \quad \text{len} = \frac{\text{Length}[c0]}{2} + 1;$$

```
c1=Table[0, {i, len}]; d1=Table[0, {i, len-2}];
c1[[1]]=c0[[Range[1, 8]]].cf1l;
c1[[2]]=c0[[Range[1, 8]]].cf2l;
d1[[1]]=c0[[Range[1, 8]]].w1l;
d1[[2]]=c0[[Range[1, 8]]].w2l;
Do[(c1[[i]]=c0[[Range[2 i-7, 2 i+6]]].cf1; c1[[i+1]]=c0[[Range[2 i-7, 2 i+6]]].cf2;), {i, 5, len-5, 4}];
c1[[len-1]]=c0[[Range[lenold-7, lenold]]].cf1r;
c1[[len]]=c0[[Range[lenold-7, lenold]]].cf2r;
Do[(c1[[i]]=c0[[Range[2 i-3, 2 i+2]]].cf3; c1[[i+1]]=c0[[Range[2 i-3, 2 i+2]]].cf4;), {i, 3, len-3, 4}];
Do[(d1[[i]]=c0[[Range[2 i-3, 2 i+10]]].w1; d1[[i+1]]=c0[[Range[2 i-3, 2 i+10]]].w2; d1[[i+2]]=c0[[Range[2 i-3, 2 i+10]]].w3; d1[[i+3]]=c0[[Range[2 i-3, 2 i+10]]].w4;), {i, 3, len-7, 4}];
d1[[len-3]]=c0[[Range[lenold-7, lenold]]].w1r;
d1[[len-2]]=c0[[Range[lenold-7, lenold]]].w2r;
```

For each element, the vector of scaling function coefficients $C_{N^*}$ from the highest level of decomposition and the concatenation of the wavelet coefficients $d_1, \ldots, d_{N^*}$ can be stored. Sample code from Mathematica™, with $N^*=9$, is shown below.

```
carbc=c9
{0, 0, 0, 0, -0.1892669811, -0.2648759611, 0.7304142708, -0.8653459287, -0.08940754894, -0.1511210853}
carbcoef=Join[d1, d2, d3, d4, d5, d6, d7, d8, d9]//Chop;
```

Next, a cubic spline is generated that interpolates the source data, and has one derivative at each data point that is equal to the slope of the line through adjacent data points. Mathematica™ has a built-in command to do this, but the algorithm for generating the spline is public domain information and readily obtainable. Sample code in Mathematica™ is shown below.

```
Clear[f1];
tmat=Transpose[temp];
Dimensions[tmat]
{2, 4096}
f1=ListInterpolation[tmat[[2]], {tmat[[1]]}]
InterpolatingFunction[{{-5.72511, 10048.6}}, "<>"]
```

This spline is then sampled in a similar manner that the elemental peak functions were sampled. Sample Mathematica™ code is shown below.

$$\text{temp} = \text{Table}\left[f1[x], \left\{x, \text{low}, \text{high}, \frac{\text{high}-\text{low}}{4096}\right\}\right];$$

len=Length[temp]
4097

The data is then padded with zeroes, and the raw data is prefiltered. The interpolation points of the function resulting from the prefiltering at the values $x_i$ are generated, and are used as a standard for comparison for changes, as opposed to the original sampled signal. Sample code for generating the interpolation points is shown below.

```
temppad=Join[temp, {0, 0, 0}]//Flatten;
c0=Join[Qlt1.temppad[[{1, 2, 3, 4}]]+Qlt2.temppad[[{5, 6,
   7, 8}]], Table[Q1.temppad[[Range[i, i+3]]]+Q2.temppad
   [[Range[i+4, i+7]]]+Q3.temppad[[Range[i+8, i+11]]], (i,
   1, len-8, 4}], Qrt1.temppad[[Range[len-4, len-1]]]+
   Qrt2.temppad[[Range[len, len+3]]]]//Flatten//Simplify//
   Chop;
trp=Table[0, {i, len}];
Do[trp[[i]]+=c0[[1]]*p11[[i]], {i, 1, 5}];
Do[trp[[i]]+=c0[[2]]*p21[[i]], {i, 1, 5}];
Do[Do[trp[[j+i]]+=c0[[j]]*p1[[i+5]], {i, -4, 4}], {j, 5, len-4,
   4}];
Do[Do[trp[[j+i-1]]+=c0[[j]]*p2[[i+5]], {i, -4, 4}], {j, 6,
   len-3, 4}];
Do[Do[trp[[j+i]]+=c0[[j]]*p3[[i+3]], {i, -2, 2}], {j, 3, len-2,
   4}];
Do[Do[trp[[j+i-1]]+=c0[[j]]*p4[[i+3]], {i, -2, 2}], {j, 4,
   len-1, 4}];
Do[trp[[len-5+i]]+=c0[[len]]p1r[[i]], {i, 1, 5}]; Do[trp[[len-
   5+i]]+=c0[[len+1]]*p2r[[i]], {i, 1, 5}];
```

The signal is then decomposed in the same manner as the data from the elemental functions, again saving the vector of scaling vector function coefficients $C_{N*}$ from the highest level of decomposition, and the concatenation of the wavelet coefficients $d_1, \ldots, d_N$.

Replacing the Wavelet Coefficients

As described in step 216 of FIG. 7, the wavelet decomposition of the test data $d_1, \ldots, d_N$, is then replaced with a linear combination of the wavelet decompositions from each element stored in the library. Sample code, with N*=9 and 5 primary elements and 16 other elements in the background, is shown below.

```
ds=nitro0val*nitro0coef+nitro1val*nitro1coef+
   nitro2val*nitro2coef+hydroval*hydrocoef+
   carbval*carbcoef+oxy0val*oxy0coef+
   oxy1val*oxy1coef+oxy2val*oxy2coef+silival*silicoef+
   unaval*unacoef+unbval*unbcoef+uncval*unccoef+
   undval*undcoef+uneval*unecoef+unfval*unfcoef+
   ungval*ungcoef+unhval*unhcoef+unival*unicoef+
   unjval*unjcoef+unkval*unkcoef+unlval*unlcoef+
   unmval*unmcoef+unnval*unncoef+unoval*unocoef+
   unpval*unpcoef;
dt1=ds[[Range[1, 2048]]];
dt2=ds[[Range[2049, 3072]]];
dt3=ds[[Range[3073, 3584]]];
dt4=ds[[Range[3585, 3840]]];
dt5=ds[[Range[3841, 3968]]];
dt6=ds[[Range[3969, 4032]]];
dt7=ds[[Range[4033, 4064]]];
dt8=ds[[Range[4065, 4080]]];
dt9=ds[[Range[4081, 4088]]];
ct9=c9;
```

As described in step 218 of FIG. 7, the signal is then reconstructed. The signal is reconstructed with as of yet undetermined variables. Mathematica™ naturally handles the symbolic algebra needed to reconstruct the signal $\tilde{c}_0$ with variables as opposed to strictly numerical amounts, but the process could be programmed into another language if necessary. Sample code for this reconstruction in Mathematica™, going from the ninth level of decomposition to the eighth level, is shown below.

```
len=Length[ct9]; lennew=2 Length[ct9]-2;
ct8=Table[0, {i, lennew}];
Do[ct8[[i]]+=ct9[[1]]*cf11[[i]]+dt9[[1]]*w11[[i]]+ct9[[2]]
   *cf21[[i]]+dt9[[2]]*w21[[i]], {i, 1, 8}];
Do[Do[ct8[[2     i+j-8]]+=ct9[[i]]*cf1[[j]]+ct9[[i+1]]*cf2
   [[j]]+dt9[[i-2]]*w1[[j]]+dt9[[i-1]]*w2[[j]]+dt9[[i]]*w3
   [[j]]+dt9[[i+1]]*w4[[j]], {j, 1, 14}], {i, 5, len-5, 4}];
Do[Do[ct8[[2 i+j-4]]+=ct9[[i]]*cf3[[j]]+ct9[[i+1]]*cf4[[j]],
   {j, 1, 6}], {i, 3, len-3, 4}];
Do[ct8[[lennew-8+i]]+=ct9[[len-1]]*cf1r[[i]]+dt9[[len-3]]
   w1r[[i]]+ct9[[len]]*cf2r[[i]]+dt9[[len-2]]*w2r[[i]], {i, 1,
   8}];
ct8=ct8//Simplify;
```

The interpolation values of this new signal are determined as before. Sample code for N=10 is shown below.

```
len=lennew-1;
new=Table[0, {i, len}];
Do[new[[i]]+=ct0[[1]]*p11[[i]], {i, 1, 5}];
Do[new[[i]]+=ct0[[2]]*p21[[i]], {i, 1, 5}];
Do[Do[new[[j+i]]+=ct0[[j]]*p1[[i+5]], {i, -4, 4}], {j, 5, len-
   4, 4}];
Do[Do[new[[j+i-1]]+=ct0[[j]]*p2[[i+5]], {i, -4, 4}], {j, 6,
   len-3, 4}];
Do[Do[new[[j+i]]+=ct0[[j]]*p3[[i+3]], {i, -2, 2}], {j, 3, len-
   2, 4}];
Do[Do[new[[j+i-1]]+=ct0[[j]]*p4[[i+3]], {i, -2, 2}], {j, 4,
   len-1, 4}];
Do[new[[len-5+i]]+=ct0[[len]]*p1r[[i]], {i, 1, 5}];
Do[new[[len-5+i]]+=ct0[[len+1]]*p2r[[i]], {i, 1, 5}];
new=new//Simplify//Chop;
```

Because the original wavelet coefficients have been replaced with a linear combination of wavelet coefficients from smoother curves, the reconstructed interpolation values will fall along a much smoother path than the original data regardless of the values associated with the variables.

Getting a Least Squares Fit

As described with step 220 of FIG. 7, a least-squares fit is calculated. In particular, a least-squares fit between the interpolation points from the original basis coefficients $c_0$ and the interpolation points from the reconstructed coefficients $\tilde{c}_0$, with respect to the variables introduced for each element is calculated. Mathematica™ has built-in routines to find the least-squares fit, but the process is in the public domain, and could be programmed into another language if necessary. Sample code, with N=10 and 5 primary elements and 16 other elements in the background, is shown below.

```
cond=Simplify[Sum[(new[[i]]-trp[[i]])^2, {i, 4097}]];
sol=NMinimize[{cond,      nitro0val≧0,      nitro1val≧0,
   nitro2val≧0,   carbval≧0,   hydroval≧0,   oxy0val≧0,
   oxy1val≧0,    oxy2val≧0,    silival≧0,    oxy2val≧0,
   unaval≧0, unbval≧0, uncval≧0, undval≧0, uneval≧0,
   unfval≧0, ungval≧0, unhval≧0, unival≧0, unjval≧0,
   unkval≧0, unlval≧0, unmval≧0, unnval≧0, unoval≧0,
   unpval≧0}, {nitro0val, nitro1val, nitro2val, hydroval, car-
   bval, oxy0val, oxy1val, oxy2val, silival, unaval, unbval,
   uncval, undval, uneval, unfval, ungval, unhval, unival,
   unjval, unkval, unlval, unmval, unnval, unoval, unpval},
   Method→"DifferentialEvolution"]
```

We set the variables to the amounts that will minimize the sum of the squares.

Identifying Compounds and Concentrations

As described with respect to step 222 of FIG. 7, compounds and concentrations of the test material may then be identified. If one is trying to identify compounds that are in the compounds library, then it may be necessary to determine whether a search is being conducted for a primary single compound in the test material, or for a mixture of the compounds. In order to get a unique solution, the number of compounds that can be in the mixture is limited to the number of elements that are being searched (not counting background elements that did not determine the analysis interval). This portion of the algorithm is based on applied linear algebra, where the angle (in degrees) between the vector of element amounts we found in the last step and the subspaces generated by vectors associated with compounds in the compounds library is identified.

To find a best single compound match the angle between the vector of amounts v that were found in the "Getting a Least Squares Fit" Section (the variables that will minimize the sum of the squares) and the vectors of ratios of elements $lib_i$ in the compounds library are found, using the formula $$\theta_i = \cos^{-1}\left(\frac{v \cdot lib_i}{\|v\|\|lib_i\|}\right).$$

The compound that corresponds to the library vector generating the smallest angle is the most prominent compound in the test material. Sample code, with res representing v, is given below.
oxyval=oxy0val+oxy1val
0.72833
o=oxyval;
c=carbval;
n1=nitro1val;
s=silival;
res={o, c, n1, s}//Chop
{0.72833, 0.710686, 0.650483, 0.0392409}
se=Table[0, {i, 1, 12}];
Do[If[res !={0, 0, 0, 0}, $$se[[i]] = \frac{180}{Pi}\text{ArcCos}\left[\frac{lib[i].res}{\sqrt{lib[i].lib[i]}\sqrt{res.res}}\right], se[[i]] = 90,$$

{i, 1, 12}];

---

Print["Angle in degrees (0 is an exact match)"];
Print["Wool/Silk →", se[[1]], If[se[[1]] == Min[se], "←", " "]];
Print["Nylon →", se[[2]], If[se[[2]] == Min[se], "←", " "]];
Print["Kevlar →", se[[3]], If[se[[3]] == Min[se], "←", " "]];
Print["Urea →", se[[4]], If[se[[4]] == Min[se], "←", " "]];
Print["RDX →", se[[5]], If[se[[5]] == Min[se], "←", " "]];
Print["TNT →", se[[6]], If[se[[6]] == Min[se], "←", " "]];
Print["C4 →", se[[7]], If[se[[7]] == Min[se], "←", " "]];
Print["Semtex →", se[[8]], If[se[[8]] == Min[se], "←", " "]];
Print["Water →", se[[9]], If[se[[9]] == Min[se], "←", " "]];
Print["Paraffin →", se[[10]], If[se[[10]] == Min[se], "←", " "]];
Print["Sand →", se[[11]], If[se[[11]] == Min[se], "←", " "]];
Print["Ammonium Nitrate →", se[[12]],
If[se[[12]] == Min[se], "←", " "]];

---

To find a mixture of k compounds in the library, with k less than or equal to the number of elements being searched the following steps may be taken. First, a list of all combinations of k elements can be generated, with no repetition. For each combination, A can be the matrix with columns formed from the k library vectors from those elements, and let b=$(b_1, \ldots, b_k)^T$ be a k-vector of coefficients for each element. Ideally, a solution to the equation Ab=v is desired, but the system is generally underdetermined (A is not invertible). To find the projection of v into the subspace spanned by the column vectors of A, $\tilde{b}=(A^TA)^{-1}A^Tv$ is calculated. The matrix $(A^TA)^{-1}A^T$ is sometimes called the pseudoinverse of the non-square matrix A. The angle between v and $\tilde{b}$ is then calculated. The percentage of each compound that is in the best-fit mixture may also be calculated. The mixture that generates the smallest angle is the most likely mixture of library compounds comprising the test material. Sample code, with res representing v, is given below.
check=Flatten[Table[{i, j}, {i, 12}, {j, i+1, 12}], 1]
{{1,2}, {1,3}, {1,4}, {1,5}, {1,6}, {1,7}, {1,8}, {1,9}, {1, 10}, {1, 11}, {1, 12}, {2, 3}, {2, 4}, {2, 5}, {2, 6}, {2, 7}, {2, 8}, {2, 9}, {2, 10}, {2, 11}, {2, 12}, {3, 4}, {3, 5}, {3, 6}, {3, 7}, {3, 8}, {3, 9}, {3, 10}, {3, 11}, {3, 12}, {4, 5}, {4, 6}, {4, 7}, {4, 8}, {4, 9}, {4, 10}, {4, 11}, {4, 12}, {5, 6}, {5, 7}, {5, 8}, {5, 9}, {5, 10}, {5, 11}, {5, 12}, {6, 7}, {6, 8}, {6, 9}, {6, 10}, {6, 11}, {6, 12}, {7, 8}, {7, 9}, {7, 10}, {7, 11}, {7, 12}, {8, 9}, {8, 10}, {8, 11}, {8, 12}, {9, 10}, {9, 11}, {9, 12}, {10, 11}, {10, 12}, {11, 12}}
name[i_:=Which[i=1, "Wool/Silk", i=2, "Nylon", i=3, "Kevlar", i=4, "Urea", i=5, "RDX", i=6, "TNT", i=7, "C4", i=8, "Semtex", i=9, "Water/Sand", i=10, "Paraffin", i=11, "Sand", i=12, "Ammonium Nitrate"];
two=Table[0, {i, Length[check]}];
Do[(A=Transpose[{lib[check[[i, 1]]], lib[check[[i, 2]]]}]1;
b=Inverse[Transpose[A].A].Transpose[A].res//FullSimplify//Chop;
If[b[[1]]<0, b[[1]]=0];
If[b[[2]]<0, b[[2]]=0];
best=A.b//FullSimplify//Chop;
If[best≠{0, 0, 0, 0} && res≠{0, 0, 0, 0}, $$angle = \text{Re}\left[\frac{180}{Pi}\text{ArcCos}\left[\frac{best.res}{\sqrt{best.best}\sqrt{res.res}}\right]\right], angle = 90;$$

$$percent1 = \text{If}\left[b \neq \{0, 0\}, \frac{b[[1]]}{b[[1]] + b[[2]]} * 100, 0\right];$$

$$percent2 = \text{If}\left[b \neq \{0, 0\}, \frac{b[[2]]}{b[[1]] + b[[2]]} * 100, 0\right];$$

two[[i]]=If[percent1≧percent2,
{name[check[[i, 1]]], percent1, name[check[[i, 2]]], percent2, angle},
{name[check[[i, 2]]], percent2, name[check[[i, 1]]], percent1, angle}];
), {i, Length[check]}];
Sort[two, #1[[5]]<#2[[5]]&]//MatrixForm

EXAMPLES

Two examples from the world of explosives detection are provided below. The elements that are being searched for are oxygen, carbon, nitrogen, and silicon (O, C, N, and Si, respectively). The independent value in both examples are keV (kilo-electron volts) and the dependent value is the gamma ray counts at each kilo-electron volt level measured. The peak locations for each element, their relative heights, and the standard deviation for each peak is given in Table 1.

TABLE 1

Gaussian peak information for the elements being searched.

| Element | Peak Location (keV) | Gamma Ray Count at Peak | FWHM |
|---|---|---|---|
| carbon (C) | 4439 | 6.77 | 11.913 |
| nitrogen (N) | 729.6 | 5.30 | 7.523 |
|  | 1634.2 | 15.22 | 3.787 |
|  | 5105 | 7.02 | 5.679 |

TABLE 1-continued

Gaussian peak information for the elements being searched.

| Element | Peak Location (keV) | Gamma Ray Count at Peak | FWHM |
|---|---|---|---|
| oxygen (O) | 5107.3 | 11.25 | 3.545 |
|  | 5618.3 | 11.40 | 3.499 |
|  | 6129.3 | 11.79 | 3.384 |
| silicon (Si) | 1778.8 | 123.43 | 2.888 |

The functions representing these four elements are $$oxy_0(x) = 11.7890745 e^{\frac{(x-6131.06)^2}{2(3.384)^2}},$$

$$oxy_1(x) = 11.40160849 e^{\frac{(x-5613.43)^2}{2(3.499)^2}},$$

$$nitro_1(x) = 15.2201501 e^{\frac{(x-1589.34)^2}{2(3.787)^2}},$$

$$carb(x) = 6.770114934 e^{\frac{(x-4439.35)^2}{2(3.5)^2}}, \text{ and}$$

$$sili(x) = 123.4301471 e^{\frac{(x-1764.66)^2}{2(2.888)^2}}.$$

The compound library contains 10 substances with linearly independent 4-vectors, giving the relative amounts of atoms each substance has of carbon, hydrogen, nitrogen, and oxygen. The relative amounts are given in Table 2 below.

TABLE 2

Relative amount of the four elements in each compound in our compound library.

| Compounds | O | C | N | Si |
|---|---|---|---|---|
| Wool/Silk | 2 | 2 | 1 | 0 |
| Nylon | 1 | 6 | 1 | 0 |
| Kevlar | 2 | 14 | 2 | 0 |
| Urea | 1 | 1 | 2 | 0 |
| RDX | 6 | 3 | 6 | 0 |
| TNT | 6 | 7 | 3 | 0 |
| C4 | 2.67 | 2.67 | 2.18 | 0 |
| Semtex | 12 | 5 | 4 | 0 |
| Water | 1 | 0 | 0 | 0 |
| Paraffin | 0 | 1 | 0 | 0 |
| Sand | 2 | 0 | 0 | 1 |
| Ammonium nitrate | 3 | 0 | 2 | 0 |

Example 1

Figure 12A:
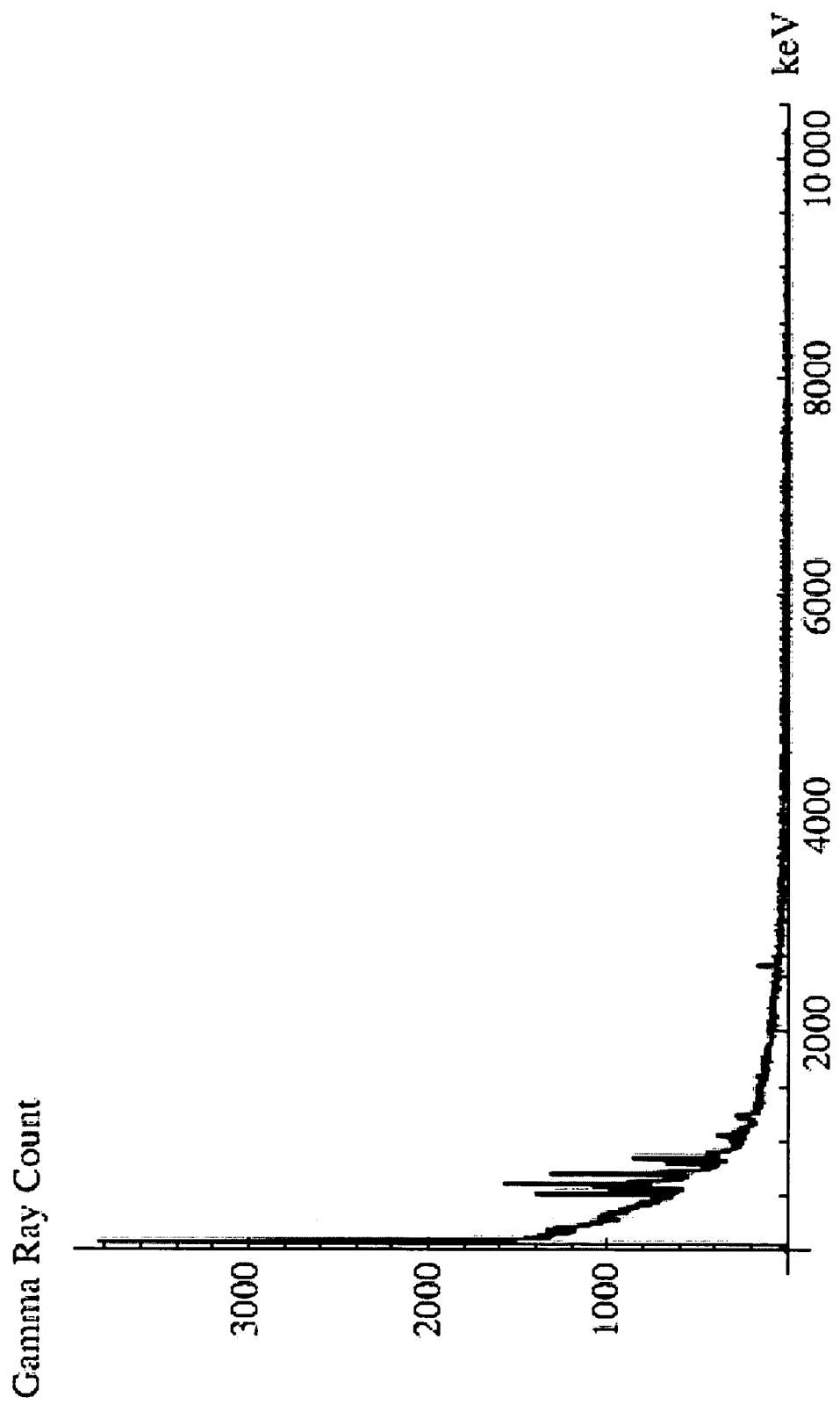
FIG. 12A illustrates sample spectral data.
Figure 12B:
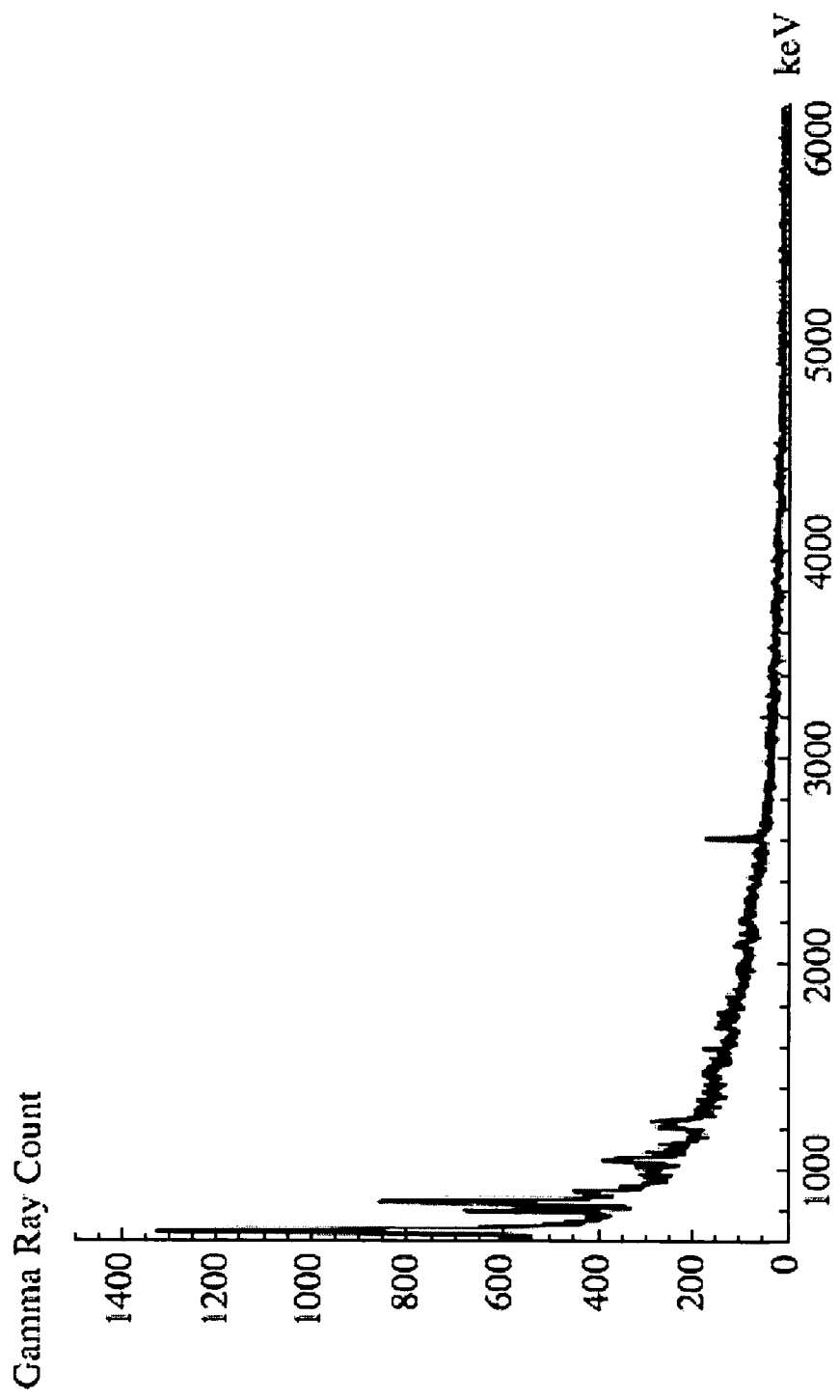
FIG. 12B illustrates the sample spectral data of FIG. 12A over an analysis window.
Figure 13:
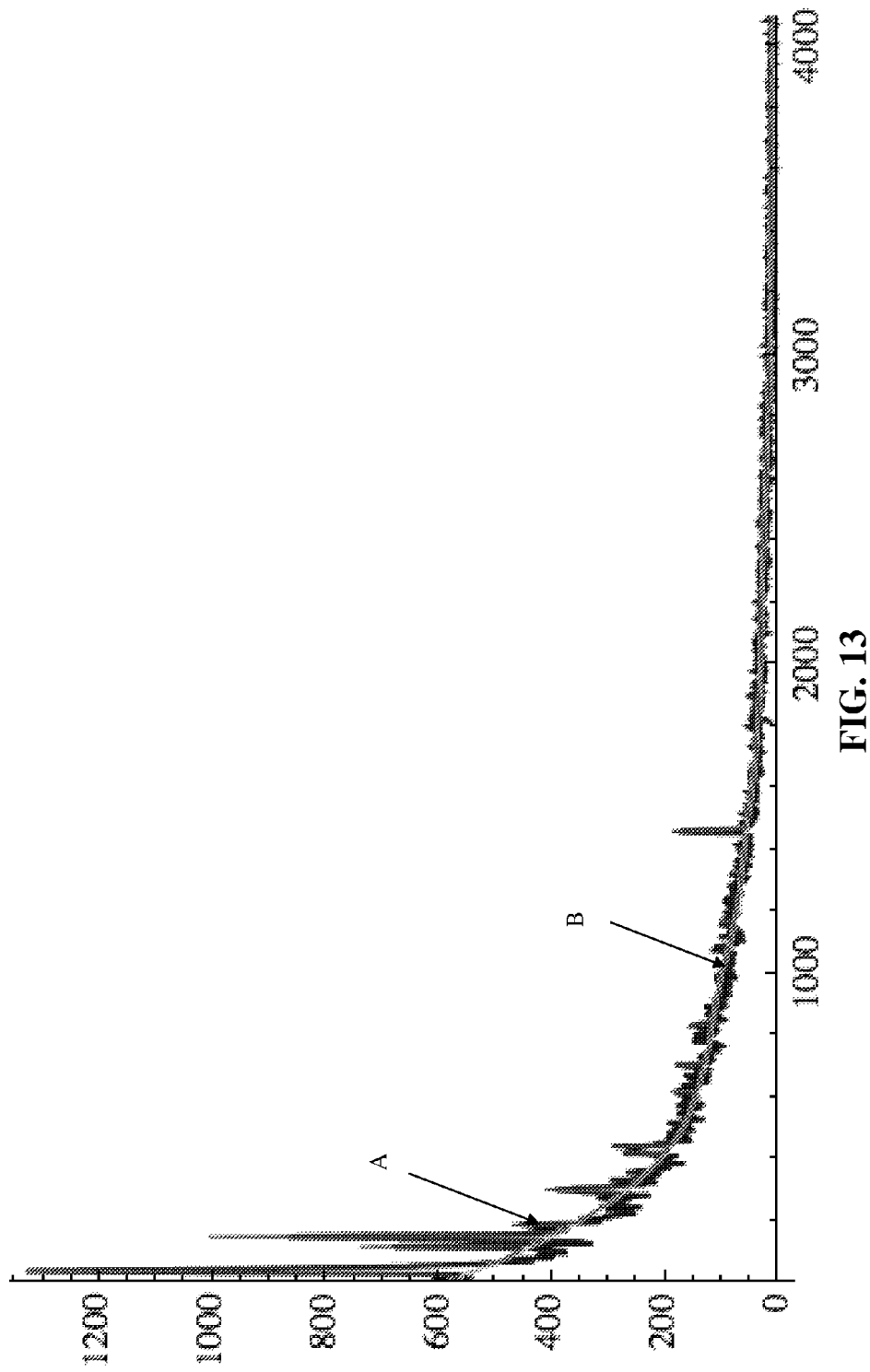
FIG. 13 illustrates the spectral data of FIG. 12A, a least squares fit curve of the spectral data, and an initial underlying curve over the analysis window of FIG. 14B.

In this first example, the data shown in FIGS. 12A and 12B is analyzed. The entire data set is shown in FIG. 12A and the data over the analysis window is shown in FIG. 12B. After decomposing the sampled signal, reconstructing with the linear combination of wavelet coefficients for each of the elements, and finding a least-squares fit, the smoother approximation shown at line A in FIG. 13 is obtained. After subtracting the equivalent amount of each of the element's scaling function coefficients, the initial "underlying curve", shown at line B in FIG. 13 is obtained.

The 4-vector {1.026453568, 1.159116984, 2.942592336, 0.352578361} is then compared with the compound library. If a single predominant compound is being searched, then the angle between the 4-vector and the stored library 4-vectors is measured as described previously. The result is shown below.

Angle in degrees (0 is an exact match)
Wool/Silk→33.6443
Nylon→53.0887
Kevlar→54.8203
Urea→8.09039←
RDX→16.9645
TNT→35.3821
C4→23.5534
Semtex→39.2659
Water→63.6185
Paraffin→65.6525
Sand→62.8273
Ammonium Nitrate→36.4148

If mixtures of two compounds are being considered, then the best approximations into the subspaces generated by the choice of compounds, and the least angles are found. The result is shown below.

| | | | | |
|---|---|---|---|---|
| Urea | 88.7613 | Sand | 11.2387 | 5.55121 |
| Urea | 98.6404 | Semtex | 1.3596 | 7.61549 |
| Urea | 89.154 | Water/Sand | 10.846 | 7.68241 |
| Urea | 95.5869 | RDX | 4.41306 | 7.68241 |
| Urea | 94.1288 | C4 | 5.87123 | 7.72334 |
| Urea | 94.0317 | Wool/Silk | 5.96827 | 7.72334 |
| Urea | 98.2923 | TNT | 1.70767 | 7.77628 |
| Urea | 96.2793 | Ammonium Nitrate | 3.72073 | 7.86535 |
| Urea | 99.3461 | Nylon | 0.653926 | 8.05535 |
| Urea | 99.7367 | Kevlar | 0.263294 | 8.05874 |
| Urea | 97.6469 | Paraffin | 2.3531 | 8.07425 |
| Paraffin | 50.6598 | RDX | 49.3402 | 15.9281 |
| RDX | 92.497 | Kevlar | 7.50297 | 15.9281 |
| RDX | 83.8451 | Nylon | 16.1549 | 15.9281 |
| RDX | 78.1444 | C4 | 21.8556 | 16.8208 |
| RDX | 100. | Ammonium Nitrate | 0 | 16.9645 |
| RDX | 100. | Sand | 0 | 16.9645 |
| RDX | 100. | Water/Sand | 0 | 16.9645 |
| RDX | 100. | Semtex | 0 | 16.9645 |
| RDX | 100. | TNT | 0 | 16.9645 |
| RDX | 100. | Wool/Silk | 0 | 16.9645 |
| C4 | 73.7521 | Ammonium Nitrate | 26.2479 | 22.0888 |
| C4 | 100. | Sand | 0 | 23.5534 |
| C4 | 100. | Paraffin | 0 | 23.5534 |
| C4 | 100. | Water/Sand | 0 | 23.5534 |
| C4 | 100. | Semtex | 0 | 23.5534 |
| C4 | 100. | TNT | 0 | 23.5534 |
| C4 | 100. | Kevlar | 0 | 23.5534 |
| C4 | 100. | Nylon | 0 | 23.5534 |
| C4 | 100. | Wool/Silk | 0 | 23.5534 |
| Ammonium Nitrate | 73.1822 | Nylon | 26.8178 | 24.12 |
| Ammonium Nitrate | 86.7319 | Kevlar | 13.2681 | 24.2882 |
| Paraffin | 64.8769 | Ammonium Nitrate | 35.1231 | 25.2845 |
| Ammonium Nitrate | 71.4828 | TNT | 28.5172 | 28.0922 |
| Wool/Silk | 60.1403 | Ammonium Nitrate | 39.8597 | 28.527 |
| Wool/Silk | 100. | Sand | 0 | 33.6443 |
| Wool/Silk | 100. | Paraffin | 0 | 33.6443 |
| Wool/Silk | 100. | Water/Sand | 0 | 33.6443 |
| Wool/Silk | 100. | Semtex | 0 | 33.6443 |
| Wool/Silk | 100. | TNT | 0 | 33.6443 |
| Wool/Silk | 100. | Kevlar | 0 | 33.6443 |
| Wool/Silk | 100. | Nylon | 0 | 33.6443 |
| TNT | 80.9608 | Semtex | 19.0392 | 34.8966 |
| TNT | 96.014 | Sand | 3.986 | 35.3796 |
| TNT | 100. | Paraffin | 0 | 35.3821 |
| TNT | 100. | Water/Sand | 0 | 35.3821 |
| TNT | 100. | Kevlar | 0 | 35.3821 |
| TNT | 100. | Nylon | 0 | 35.3821 |
| Ammonium Nitrate | 88.8366 | Semtex | 11.1634 | 35.5731 |

-continued

| | | | | |
|---|---|---|---|---|
| Ammonium Nitrate | 100. | Sand | 0 | 36.4148 |
| Ammonium Nitrate | 100. | Water/Sand | 0 | 36.4148 |
| Semtex | 53.41 | Nylon | 46.59 | 36.6527 |
| Semtex | 74.4896 | Kevlar | 25.5104 | 36.921 |
| Paraffin | 73.6053 | Semtex | 26.3947 | 38.1596 |
| Semtex | 100. | Sand | 0 | 39.2659 |
| Semtex | 100. | Water/Sand | 0 | 39.2659 |
| Sand | 65.5957 | Nylon | 34.4043 | 44.9894 |
| Water/Sand | 80.1843 | Nylon | 19.8157 | 45.8997 |
| Sand | 82.5566 | Kevlar | 17.4434 | 46.023 |
| Water/Sand | 90.9967 | Kevlar | 9.00325 | 46.9012 |
| Paraffin | 66.8725 | Sand | 33.1275 | 52.0308 |
| Water/Sand | 51.8723 | Paraffin | 48.1277 | 52.6888 |
| Nylon | 100. | Paraffin | 0 | 53.0887 |
| Nylon | 100. | Kevlar | 0 | 53.0887 |
| Kevlar | 100. | Paraffin | 0 | 54.8203 |
| Water/Sand | 57.5286 | Sand | 42.4714 | 62.3758 |

The Example 1 spectra was, in fact, generated from a urea test sample.

Example 2

Figure 14A:
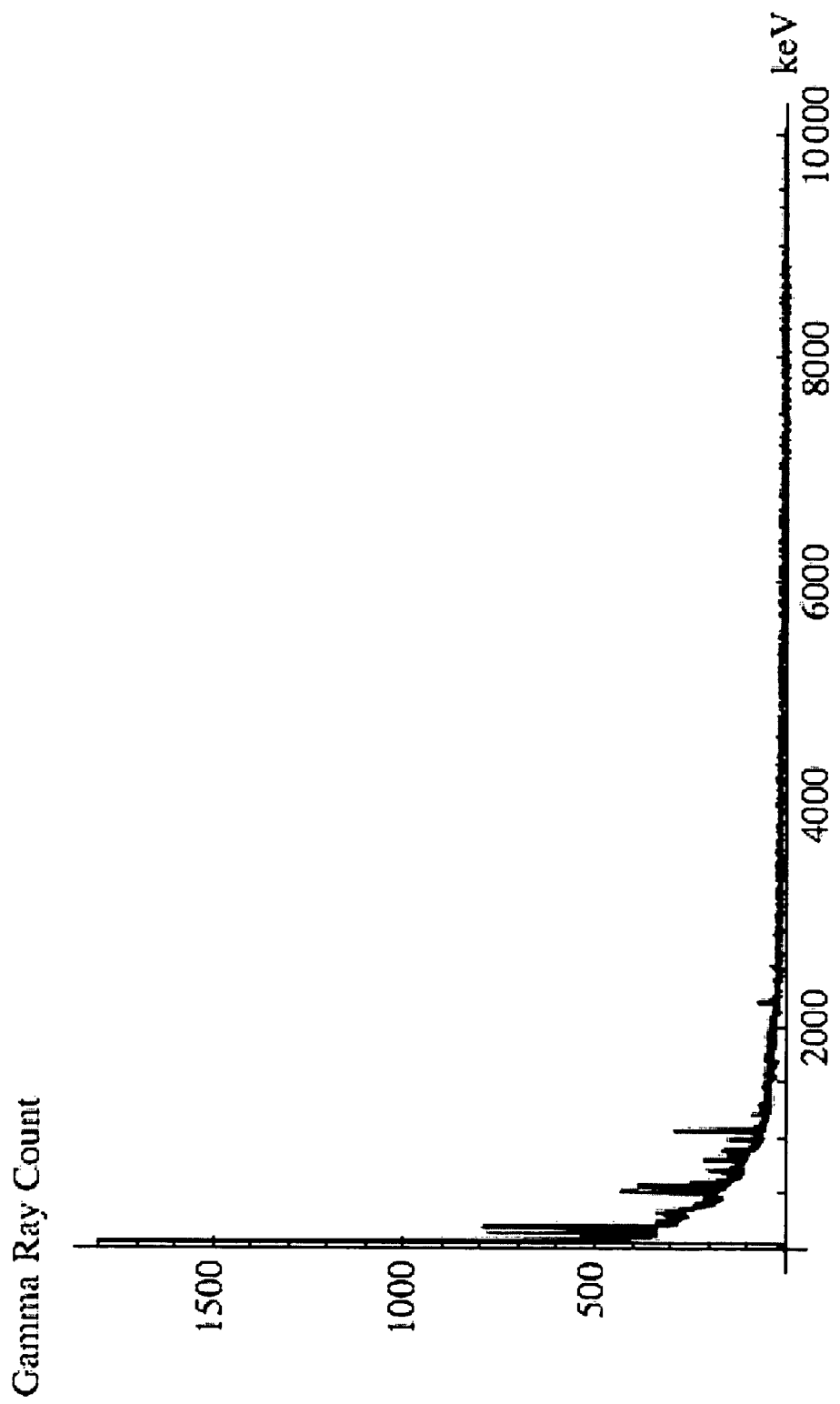
FIG. 14A illustrates sample spectral data.
Figure 14B:
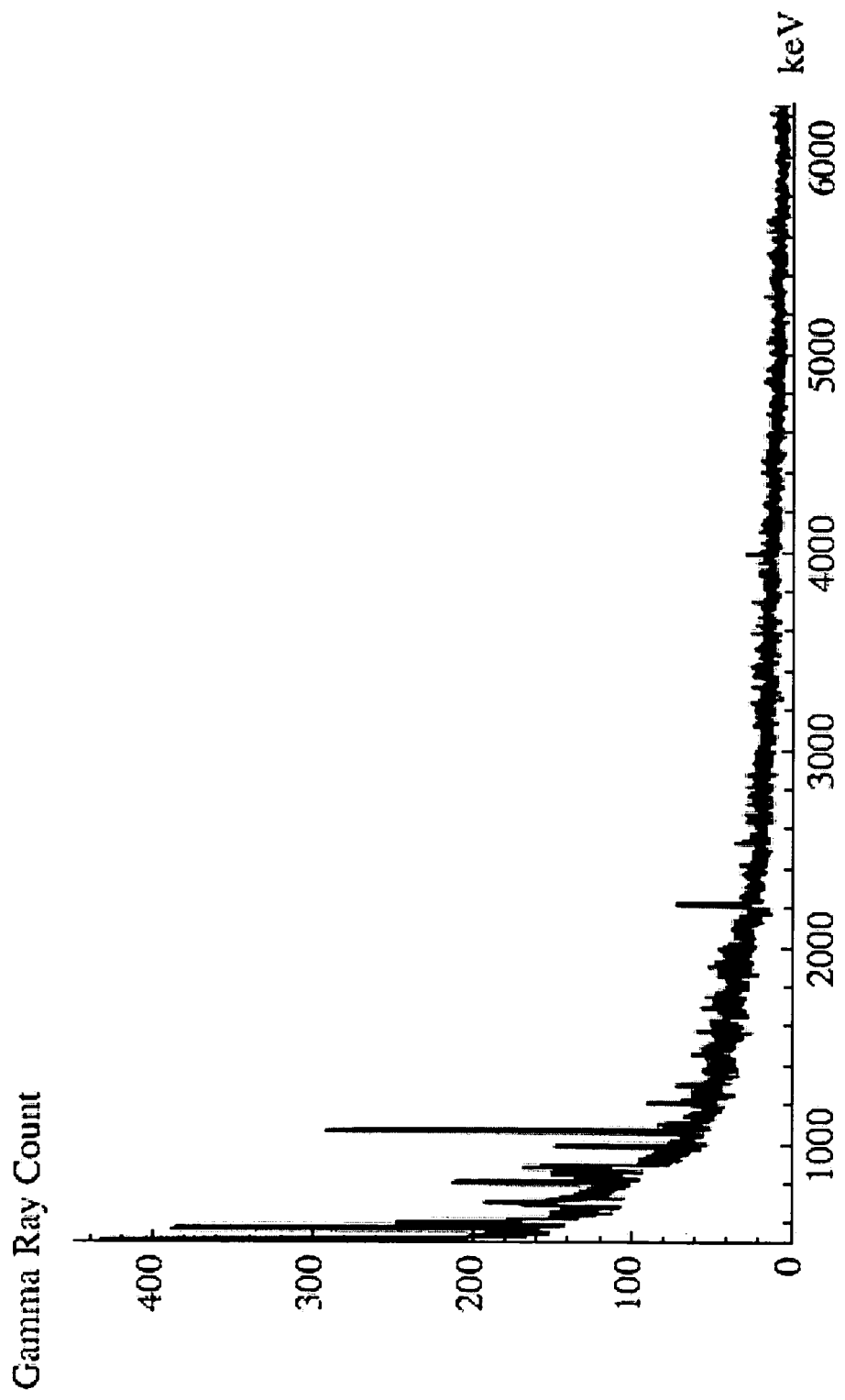
FIG. 14B illustrates the sample spectral data of FIG. 14A over an analysis window.
Figure 15:
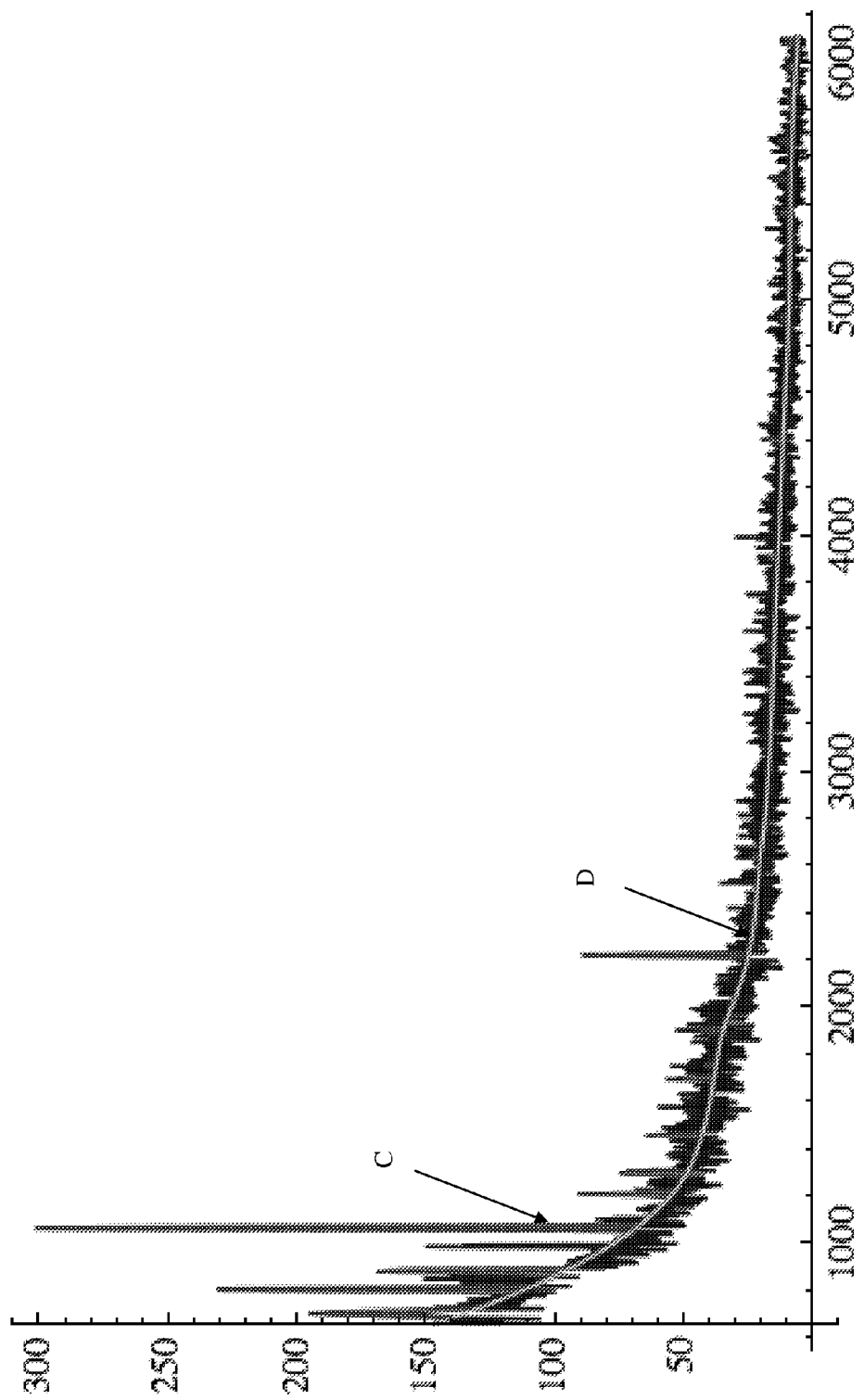
FIG. 15 illustrates the spectral data of FIG. 14A, a least squares fit curve of the spectral data, and an initial underlying curve over the analysis window of FIG. 14B.

In this second example, the data shown in FIGS. 14A and 14B is analyzed. The entire data set is shown in FIG. 14A and the data over the analysis window is shown in FIG. 14B. After decomposing the sampled signal, reconstructing with the linear combination of wavelet coefficients for each of the elements, and finding a least-squares fit, the smoother approximation shown at line C in FIG. 15 is obtained. After subtracting the equivalent amount of each of the element's scaling function coefficients, the initial "underlying curve", shown at line D in FIG. 15 is obtained.

The 4-vector {0.7283295874, 0.7106862386, 0.6504828834, 0.03924085654} is then compared with the compound library. If a single predominant compound is being searched, then the angle between the 4-vector and the stored library 4-vectors is measured as described previously. The result is shown below.
Angle in degrees (0 is an exact match)
Wool/Silk→13.2604
Nylon→40.7522
Kevlar→42.5866
Urea→22.2276
RDX→16.9164
TNT→15.3797
C4→3.24337←
Semtex→25.0054
Water→52.9345
Paraffin→53.9758
Sand→56.3844
Ammonium Nitrate→36.8606

If we wish to consider mixtures of two of the compounds, then we find best approximations into the subspaces generated by the choice of compounds, and find the least angles. The result is shown below.

| | | | | |
|---|---|---|---|---|
| C4 | 82.414 | Urea | 17.586 | 1.95275 |
| Wool/Silk | 57.5575 | Urea | 42.4425 | 1.95275 |
| C4 | 93.9053 | RDX | 6.09467 | 2.37145 |
| C4 | 95.4662 | Ammonium Nitrate | 4.53382 | 2.95083 |
| Paraffin | 76.1063 | RDX | 23.8937 | 3.20697 |
| RDX | 78.9387 | Kevlar | 21.0613 | 3.20697 |
| RDX | 60.9385 | Nylon | 39.0615 | 3.20697 |

-continued

| | | | | |
|---|---|---|---|---|
| C4 | 98.1364 | Sand | 1.86358 | 3.20999 |
| C4 | 100. | Water/Sand | 0 | 3.24337 |
| C4 | 100. | Nylon | 0 | 3.24337 |
| C4 | 100. | Wool/Silk | 0 | 3.24337 |
| C4 | 100. | Paraffin | 0 | 3.24337 |
| C4 | 100. | TNT | 0 | 3.24337 |
| C4 | 100. | Semtex | 0 | 3.24337 |
| C4 | 100. | Kevlar | 0 | 3.24337 |
| Urea | 73.1997 | TNT | 26.8003 | 3.71397 |
| TNT | 50.7116 | RDX | 49.2884 | 5.01018 |
| Ammonium Nitrate | 65.0841 | Nylon | 34.9159 | 5.28986 |
| Ammonium Nitrate | 81.756 | Kevlar | 18.244 | 5.50077 |
| Wool/Silk | 80.1115 | RDX | 19.8885 | 6.46718 |
| Paraffin | 72.6052 | Ammonium Nitrate | 27.3948 | 6.78338 |
| TNT | 52.763 | Ammonium Nitrate | 47.237 | 10.6647 |
| Wool/Silk | 85.1127 | Ammonium Nitrate | 14.8873 | 11.3021 |
| Urea | 86.5674 | Semtex | 13.4326 | 11.6206 |
| Wool/Silk | 100. | Sand | 0 | 13.2604 |
| Wool/Silk | 100. | Paraffin | 0 | 13.2604 |
| Wool/Silk | 100. | Water/Sand | 0 | 13.2604 |
| Wool/Silk | 100. | Semtex | 0 | 13.2604 |
| Wool/Silk | 100. | TNT | 0 | 13.2604 |
| Wool/Silk | 100. | Kevlar | 0 | 13.2604 |
| Wool/Silk | 100. | Nylon | 0 | 13.2604 |
| TNT | 85.0179 | Semtex | 14.9821 | 14.5703 |
| TNT | 88.3922 | Sand | 11.6078 | 15.3155 |
| TNT | 90.993 | Water/Sand | 9.00703 | 15.3731 |
| TNT | 100. | Paraffin | 0 | 15.3797 |
| TNT | 100. | Kevlar | 0 | 15.3797 |
| TNT | 100. | Nylon | 0 | 15.3797 |
| RDX | 84.0383 | Semtex | 15.9617 | 16.0269 |
| Urea | 85.2908 | Nylon | 14.7092 | 16.1548 |
| Urea | 93.4273 | Kevlar | 6.57269 | 16.367 |
| Nylon | 53.9319 | Semtex | 46.0681 | 16.6108 |
| Urea | 55.2402 | Water/Sand | 44.7598 | 16.6869 |
| RDX | 58.7394 | Urea | 41.2606 | 16.6869 |
| RDX | 100. | Ammonium Nitrate | 0 | 16.9164 |
| RDX | 100. | Sand | 0 | 16.9164 |
| RDX | 100. | Water/Sand | 0 | 16.9164 |
| Semtex | 67.6959 | Kevlar | 32.3041 | 16.9555 |
| Urea | 75.3904 | Sand | 24.6096 | 17.4039 |
| Urea | 57.1081 | Paraffin | 42.8919 | 17.4648 |
| Paraffin | 83.4043 | Semtex | 16.5957 | 18.7673 |
| Urea | 86.5998 | Ammonium Nitrate | 13.4002 | 21.2398 |
| Semtex | 100. | Ammonium Nitrate | 0 | 25.0054 |
| Semtex | 100. | Sand | 0 | 25.0054 |
| Semtex | 100. | Water/Sand | 0 | 25.0054 |
| Water/Sand | 81.7628 | Nylon | 18.2372 | 25.8175 |
| Water/Sand | 91.63 | Kevlar | 8.37001 | 26.801 |
| Sand | 64.365 | Nylon | 35.635 | 28.3183 |
| Sand | 81.547 | Kevlar | 18.453 | 29.4437 |
| Water/Sand | 50.613 | Paraffin | 49.387 | 32.6349 |
| Paraffin | 70.3743 | Sand | 29.6257 | 36.1278 |
| Ammonium Nitrate | 100. | Sand | 0 | 36.8606 |
| Ammonium Nitrate | 100. | Water/Sand | 0 | 36.8606 |
| Nylon | 100. | Paraffin | 0 | 40.7522 |
| Nylon | 100. | Kevlar | 0 | 40.7522 |
| Kevlar | 100. | Paraffin | 0 | 42.5866 |
| Water/Sand | 94.3054 | Sand | 5.6946 | 52.8717 |

The spectra was, in fact, generated from a test sample of a mixture meant to simulate the explosive C4.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

I claim:

1. A method of pre-filtering and analyzing spectral data for the detection of elemental signatures in an interrogated object using multi-wavelet filters implemented on a computer having memory and one or more processors, comprising:

electronically receiving into said memory data of gamma ray counts obtained from bombardment of an interrogated object;

pre-filtering, utilizing said one or more processors, said data of gamma ray counts in order to maintain polynomial order using a quasi-interpolation pre-filter, said pre-filtering converting said data into pre-filtered signal data;

generating, utilizing said one or more processors, an orthogonal scaling vector $\Phi=(\phi_1,\phi_2,\phi_3,\phi_4)^T$, wherein $\phi_1$, $\phi_2$, $\phi_3$, and $\phi_4$ represent individual elements of said orthogonal scaling vector $\Phi$, to construct filters for multi-wavelet decomposition of said pre-filtered signal data, said orthogonal scaling vector $\Phi=(\phi_1,\phi_2,\phi_3,\phi_4)^T$ substantially satisfying a dilation equation defined by:

$$\Phi(x) = \sqrt{2} \sum_{i=-2}^{1} g_i \Phi(2x-i)$$

wherein $g_i$ represents matrix coefficients of said orthogonal scaling vector $\Phi$, wherein i is a counter of a summation and represents whole numbers from −2 to 1, inclusive, and wherein x is an independent variable and represents real numbers, and having left boundary functions for $\phi_1$ and $\phi_2$ defined by:

$$\phi_1^L = \frac{\phi_1 R\big|_{[0,1]} - \frac{\langle \phi_1|_{[0,1]}, \phi_2|_{[0,1]}\rangle}{\langle \phi_2|_{[0,1]}, \phi_2|_{[0,1]}\rangle}\phi_2 \big|_{[0,1]}}{\left\|\phi_1\big|_{[0,1]} - \frac{\langle \phi_1|_{[0,1]}, \phi_2|_{[0,1]}\rangle}{\langle \phi_2|_{[0,1]}, \phi_2|_{[0,1]}\rangle}\phi_2\right\|_{[0,1]}} \text{ and } \phi_2^L = \sqrt{2}\,\phi_2\big|_{[0,1]}$$

and right boundary functions for $\phi_1$ and $\phi_2$ defined by:

$\phi_1^R(x) = \phi_1^L(1-x)$ and $\phi_2^R(x) = -\phi_2^L(1-x)$, constructing, utilizing said one or more processors, a multi-wavelet $\Psi = (\psi_1, \psi_2, \psi_3, \psi_4)^T$ for said scaling vector $\Phi = (\phi_1, \phi_2, \phi_3, \phi_4)^T$, said multi-wavelet $\Psi$ associated with said orthogonal scaling vector $\Phi = (\phi_1, \phi_2, \phi_3, \phi_4)^T$, wherein $\psi_1$, $\psi_2$, $\psi_3$, and $\psi_4$ are individual elements of said multi-wavelet $\Psi$ and substantially satisfy a dilation equation defined by:

$$\Psi(x) = \sqrt{2}\sum_{i=-2}^{1} h_i \Phi(2x - i)$$

wherein $h_i$ represents matrix coefficients of $\Psi$, said multi-wavelet elements $\psi_1$ and $\psi_2$ having a left boundary dilation equation defined by:

$$\begin{bmatrix}\psi_1^L \\ \psi_2^L\end{bmatrix}(x) = h_0^L \begin{bmatrix}\phi_1^L \\ \phi_2^L \\ \phi_3 \\ \phi_4\end{bmatrix}(2x) + h_1^L \Phi(2x - i)$$

and a right boundary dilation equation defined by:

$$\begin{bmatrix}\psi_1^R \\ \psi_2^R\end{bmatrix}(x) = h_0^R \Phi(2x) + h_1^R \Phi(2x-1) + h_2^R\begin{bmatrix}\phi_1^R \\ \phi_2^R\end{bmatrix}(2x-1); \text{ and}$$

interpolating, utilizing said one or more processors, said multi-wavelet $\Psi$ for comparison with an elemental database to identify elements and element concentrations in said interrogated object.

2. The method of claim 1 wherein said pre-filtered signal data is decomposed to a user selected level of decomposition utilizing said multi-wavelet.

3. The method of claim 2 wherein said user selected level of decomposition is based on the curvature of underlying background distortion of said data.

4. The method of claim 2 wherein said level of decomposition is bound by a maximum level of decomposition.

5. The method of claim 1 wherein said elements include oxygen, nitrogen, carbon, and silicon.

6. The method of claim 1 wherein said elemental database includes said elemental concentrations corresponding to C4 and TNT.

7. A method for determining elements of an interrogated object implemented on a computer having memory and one or more processors, comprising:
   storing a library database of response spectra for various elements of interest;
   irradiating an object to create neutron reactions;
   generating a data spectrum by detecting the gamma rays emitted by said object;
   recognizing the individual elements contained in said data spectrum by the following steps:
   generating, utilizing said one or more processors, an orthogonal scaling vector $\Phi = (\phi_1, \phi_2, \phi_3, \phi_4)^T$, wherein $\phi_1$, $\phi_2$, $\phi_3$, and $\phi_4$ represent individual elements of said orthogonal scaling vector $\Phi$, to construct filters for wavelet decomposition, said orthogonal scaling vector $\Phi$ satisfying the dilation equation:

$$\Phi(x) = \sqrt{2}\sum_{i=-2}^{1} g_i \Phi(2x - i)$$

wherein $g_i$ represents matrix coefficients of said orthogonal scaling vector $\Phi$, wherein i is a counter of a summation in said dilation equation and represents whole numbers from −2 to 1, inclusive, wherein x is an independent variable and represents real numbers, and wherein said filters are orthogonal multi-wavelet filters;
   creating, utilizing said one or more processors, an analysis window for said elements of interest;
   pre-filtering, utilizing said one or more processors, said data spectrum over said analysis window, thereby creating an original data set;
   decomposing, utilizing said one or more processors, said original data set utilizing said orthogonal multiwavelet filters to a level of decomposition, thereby creating a wavelet decomposition data set;
   replacing, utilizing said one or more processors, said wavelet decomposition data set with a calculated linear combination of a wavelet decomposition for each of said elements of interest, thereby creating an altered decomposed data set;
   reconstructing, utilizing said one or more processors, said altered decomposed data set, thereby creating a reconstructed data set;
   determining, utilizing said one or more processors, coefficients that minimize the sum of the squares of the differences between interpolation points of the reconstructed data set and interpolation points of the original data set;
   creating, utilizing said one or more processors, a least squares fit between interpolation points of said original data set and said reconstructed data set based on said coefficients;
   converting, utilizing said one or more processors, said least squares fit into a set of basis coefficients to create a vector of element amounts showing the relative amounts of each of said elements of interest in said test material; and
   identifying, utilizing said one or more processors, the angle θ between said vector of element amounts and at least one of vectors associated with said elements of interest and subspaces generated by said vectors associated with said elements of interest.

8. The method of claim 7 wherein said angle θ is found by θ=cos$^{-1}$ [(said vector of element amounts·said vectors associated with said elements of interest)/(‖said vector of element amounts‖‖said vectors associated with said elements of interest‖)].

9. The method of claim 7 wherein said level of decomposition is a user inputted level of decomposition.

10. The method of claim 9 wherein said level of decomposition is bound by a maximum level of decomposition.

11. The method of claim 9 further comprising adjusting a peak center of at least one of said elements of interest.

12. The method of claim 11 wherein said step of adjusting a peak center of at least one of said elements of interest includes calculating a center of mass of an adjusted elemental spectra data set.

13. The method of claim 12 wherein said adjusted elemental spectra data set is generated by subtracting decomposed elemental spectra data set from original elemental spectra data set, wherein said decomposed elemental spectra data set is obtained utilizing said orthogonal multiwavelet filters.

14. A method for determining elements in spectral data corresponding to an interrogated object implemented on a computer, said computer having memory and one or more processors, comprising:
    storing a library database of response spectra for various elements of interest;
    adjusting, utilizing said one or more processors, a peak center of at least one of said elements of interest;
    storing, utilizing said one or more processors, a level of decomposition;
    receiving, utilizing said one or more processors, raw spectral data corresponding to properties of an object interrogated at a plurality of energy levels;
    pre-filtering, utilizing said one or more processors, a sample from a spline that interpolates said raw spectral data, thereby creating an original data set;
        wherein said pre-filtering utilizes a non-orthogonal quasi-interpolation pre-filter;
    decomposing said original data set to said level of decomposition, thereby creating a wavelet decomposition data set;
        wherein said decomposing utilizes orthogonal multiwavelet filters;
    replacing, utilizing said one or more processors, said wavelet decomposition data set with a calculated linear combination of a wavelet decomposition for each of said elements of interest, thereby creating an altered decomposed data set;
    reconstructing, utilizing said one or more processors, said altered decomposed data, thereby creating a reconstructed data set;
    determining, utilizing said one or more processors, coefficients that minimize the sum of the squares of the differences between interpolation points of the reconstructed data set and interpolation points of the original data set;
    creating, utilizing said one or more processors, a least squares fit between interpolation points of said original data and said reconstructed data based on said coefficients;
    converting, utilizing said one or more processors, said least squares fit into a set of basis coefficients to create a vector of element amounts showing the relative amounts of each of said elements of interest in said test material; and
    identifying, utilizing said one or more processors, the angle $\theta$ between said vector of element amounts and at least one of vectors associated with said elements of interest and subspaces generated by said vectors associated with said elements of interest.

15. The method of claim 14 wherein said step of adjusting a peak center of at least one of said elements of interest includes calculating a center of mass of adjusted elemental spectra data.

16. The method of claim 15 wherein said adjusted elemental spectra data is generated by subtracting decomposed elemental spectra data from original elemental spectra data, wherein said decomposed elemental spectra data is obtained utilizing said orthogonal multiwavelet filters.

17. The method of claim 16 wherein angle $\theta$ is found by $\theta = \cos^{-1}[(\text{said vector of element amounts} \cdot \text{said vectors associated with said elements of interest})/(\|\text{said vector of element amounts}\| \|\text{said vectors associated with said elements of interest}\|)]$.

18. The method of claim 17 wherein said level of decomposition is a user inputted level of decomposition.

19. The method of claim 14 of wherein said energy levels include a plurality of frequency levels.

* * * * *